(12) United States Patent
Elend et al.

(10) Patent No.: US 8,956,838 B2
(45) Date of Patent: Feb. 17, 2015

(54) CARBOXYL ESTERASE POLYPEPTIDES

(75) Inventors: Christian Elend, Friedland (DE);
Karl-Erich Jaeger, Mulheim (DE);
Christian Leggewie, Essen (DE);
Christel Vollstedt, Tornesch (DE);
Wolfgang Streit, Monkeberg (DE)

(73) Assignee: B.R.A.I.N., Zwingenberg (DE)

( * ) Notice: Subject to any disclaimer, the term of this patent is extended or adjusted under 35 U.S.C. 154(b) by 1192 days.

(21) Appl. No.: 12/298,874

(22) PCT Filed: Apr. 27, 2007

(86) PCT No.: PCT/EP2007/003772
§ 371 (c)(1),
(2), (4) Date: May 5, 2009

(87) PCT Pub. No.: WO2007/128441
PCT Pub. Date: Nov. 15, 2007

(65) Prior Publication Data
US 2009/0221031 A1    Sep. 3, 2009

(30) Foreign Application Priority Data
Apr. 28, 2006 (EP) .................................. 06008953

(51) Int. Cl.
| C12P 7/02 | (2006.01) |
| C12N 9/18 | (2006.01) |
| C12N 15/00 | (2006.01) |
| C12N 1/20 | (2006.01) |
| C12N 15/74 | (2006.01) |
| C07H 21/04 | (2006.01) |

(52) U.S. Cl.
CPC ........................ *C12N 9/18* (2013.01)
USPC ...... 435/155; 435/197; 435/320.1; 435/252.3; 435/471; 435/252.31; 435/252.33; 435/252.34; 435/252.35; 536/23.2; 536/23.7; 536/23.4

(58) Field of Classification Search
CPC .......................... C12N 9/18; C12Y 301/01001
USPC ........................................................... 435/197
See application file for complete search history.

(56) References Cited

FOREIGN PATENT DOCUMENTS

EP    0749980 A1 * 12/1996

OTHER PUBLICATIONS

Alexson et al., J. Biol. Chem. 269:17118-17124, 1994.*
GenBank Accession No. P10959, Feb. 1997, 4 pages.*
Leggewie, C., Dissertation, "New biocatalysts from the metagenome: Expression, identification and biochemical properties", Düsseldorf, Jul. 2005.*
Steele et al., J. Mol. Microbiol. Biotechnol. 16:25-37, 2009.*
Nishizawa et al., Appl. Environmen. Microbiol. 61:3208-3215, 1995.*
IUBMB Enzyme Nomenclature for EC. 3.1.1.1, obtained from www.chem.qmul.ac.uk/iubmb/enzyme/EC3/1/1/1.html, 2 pages, last viewed Sep. 19, 2011.*
Arpigny, Jean Louis, et al., Bacterial Lipolytic Enzymes: Classification and Properties, Biochem. J., 343:177-183 (1999).
Elend, C., et al., Isolation and Biochemical Characterization of Two Novel Metagenome-Derived Esterases, Applied and Environmental Microbiology, 72(5):3637-3645 (2006).
Wagner, Ulrike G., et al., EstB from *Burkholderia gladioli*: A novel esterase with a β-lactamase fold reveals steric factors to discriminate between esterolytic and β-lactam cleaving activity, Protein Science, 11:467-478 (2002).
Database EMBL [Online], May 19, 2006 XP002448744 retrieved from EMBL accession No. CP000356 Database accession No. CP000356 abstract.

* cited by examiner

*Primary Examiner* — David J Steadman
(74) *Attorney, Agent, or Firm* — Pillsbury Winthrop Shaw Pittman LLP

(57) ABSTRACT

The present invention relates to a polynucleotide encoding an enzyme having carboxyl esterase [E.C. 2.1.1.1] activity.

19 Claims, 12 Drawing Sheets

Figure 1

```
ATGAGCGCCGAAGAACTAGGGTTCCTGCCCGACCGCCTAGCGCGGATCAGCGATCATATC
CAGACCAACTATCTCGACAATGGCAAGCTGCCTTTTGCGTCGCTGCTGATCGGTCGCGGC
GACGACATCGCCCTGCAATGGAGTTCGGGCGTCGCCGACGATGCTATTTTCCGCATTGCA
TCGATGACCAAACCGGTCACCTCGGTTGCGTTCATGCAACTGGTCGAACAGGGCAAAGTC
GCCCTGACCGACCCGGTCGCCAAGTATATCCCCGAATTTGCCAAGCTCGGCGTTTTCGTT
GCCGGCGGCGGCAATATACCCTTTGTCAGTCGCCCGCCGACAATGCCGATGCGGATTGTC
GATGTGTTGCGGCACACAACGGGTTTTACCTATAGCTTTCAGGAACGAAGCAACATCGAC
GCGGCCTACCGGAAGACCGATGTCGAGAGCTGGACAAGAAGCACGTCACAGAGCTTCATC
GACACGCTGGCTGAAATCCCGCTCGAGTTCGACCCTGGCACGCAGTGGAATTATTCGGTT
TCGACCGATGTATTGGGCATATTGATCGAGCGAATCAGCGGGCAATCGCTTCCTGACTAT
TTCCGCGACCATATCTTCGCGCCGCTCGGGATGGTCGACACGTGCTTTACCGTTCCCGCC
GACAAGGCAGCGCGAATCCCGCAATGCTTTGCCTTCGACCCGGCAACCAAAATGAAATTG
TTCGATGAAGCTGGCGCAAGTAGCCTGTGGACCAAAGGCTGGTCGTTCAATTCAGGCGGA
GGCGGGCTGGCTTCGAGCGTCGCGGATTATCACCGGTTCTGCCGGATGCTGCTGAACGGC
GGCGCACTTGACGGTATCCAGATCATCAGCCCGAAAACACTCGAACTGATGACCGCCAAC
CATTTACCGGGCGGGCAAGACCTCACGCAAATGTCGAAATCCTTGTTCAGCGAGGCCGAA
ATGGCGGGCATCGGCTTTGGCCTGGGTTTTGCCACCACGATCGATAGCGTAGCGACGCTC
ACCCCATGCTCTACGGGCGATTTTTACTGGGGCGGCATGTATTCGACCGCGTTCTTCGTC
GATCCGGTCGAGGATATCATCATGATCTTTATGACTCAATTGATGCCGTCGAGCACCTAT
CCGGTGCGGCGCGAAATCAAGACGATGATCTACAGCGCGCTCGCCGCCTAA
```

Figure 2

```
MSAEELGFLPDRLARISDHIQTNYLDNGKLPFASLLIGRGDDIALQWSSGVADDAIFRIA
SMTKPVTSVAFMQLVEQGKVALTDPVAKYIPEFAKLGVFVAGGGNIPFVSRPPTMPMRIV
DVLRHTTGFTYSFQERSNIDAAYRKTDVESWTRSTSQSFIDTLAEIPLEFDPGTQWNYSV
STDVLGILIERISGQSLPDYFRDHIFAPLGMVDTCFTVPADKAARIPQCFAFDPATKMKL
FDEAGASSLWTKGWSFNSGGGGLASSVADYHRFCRMLLNGGALDGIQIISPKTLELMTAN
HLPGGQDLTQMSKSLFSEAEMAGIGFGLGFATTIDSVATLTPCSTGDFYWGGMYSTAFFV
DPVEDIIMIFMTQLMPSSTYPVRREIKTMIYSALAA
```

Figure 3

ATGTCGATAGCGGATCAGTCATTAGCAAAAAGAGTGCAGGGCGTTAGCCAACAGGCGATT
GATGAAGGGCGTATCGTTGGCAGCGTGGTGCTGATCGCTCGGCACGGTCGCGTGATTTAC
GCCAATGCCAGCGGCTATGCCGATCGTGAACAGAAGAAACCTATGGTGCGTGAGACCCAA
TTTCGGCTGTCGTCGGTGTCCAAGCCTTATATTACGCTGGCGGCCATGCGTATGATCGAA
CAGCAGAAGCTGGGGCTGGATGATACCGTCAGCCGTTGGTTGCCGTGGTTTACCCCGGCG
CTGGCCGATGGGGTTCGCCCGCCAATTAAAATCCGTCACTTGTTGAGCCACACTGCCGGC
CTGGATTATCGTTTGAGCCAACCTGCGGAAGGACCGTATCATCGACTCGGTATTAAAGAC
GGTATGGAACTGTCGTCGTTAACGCTGGAACAGAATCTGCGCCTGTTGGCGCAGGCGGAT
CTGTTGGCCGAGCCGGGCAGCGAGTTTCGATATTCACTGGCAATCGATGTGCTGGGGGCG
GTGCTGGAACAGGTGGCGGGCGAGCCCTTGCCGCAGGTGTTCAACCATTGGGTTGCCCAA
CCTTTGGGGTTGCGTAATACCGGTTTTTACACCACCGATGTCGATAATCTGGCAACGGCG
TATCACGACACCGCCGCGGAGCCGGAACCTATACGAGATGGCATGTTGCTGACCCTGCCG
GAAGGGTTCGGCTTCGAGATTGAACTGGCACCCTCGCGCGCACTGGACGCTCAGGCCTAT
CCTTCTGGCGGCGCTGGCATGGTCGGCGATGCAGACGATGTGTTGCAGTTGGTGGAAACC
TTGCGCACTGGCAAGGAAGGCATTTTACAGCCGGCCACCGCAGCGCTGATGCGTCAAGCG
CATGTCGGGTCGCACGCCGAGACTCAGGGGCCCGGCTGGGGGTTTGGTTTCGGCGGTGCG
GTACTGGAAGATGCGCAGTTGGCGGCGACGCCTCAGCACAATGGCACTCTGCAGTGGGGC
GGTGTCTATGGCCACAGTTGGTTTTACGATCCGCAAGCGGCGATCAGCGTGGTAGCCTTG
ACCAATACGGCCTTTGAAGGCATGAGTGGACGTTATCCACTGCAAATCCGCGATGCTGTT
TACGGGACAAACGAACCTACTCGCTAA

Figure 4

MSIADQSLAKRVQGVSQQAIDEGRIVGSVVLIARHGRVIYANASGYADREQKKPMVRETQ
FRLSSVSKPYITLAAMRMIEQQKLGLDDTVSRWLPWFTPALADGVRPPIKIRHLLSHTAG
LDYRLSQPAEGPYHRLGIKDGMELSSLTLEQNLRLLAQADLLAEPGSEFRYSLAIDVLGA
VLEQVAGEPLPQVFNHWVAQPLGLRNTGFYTTDVDNLATAYHDTAAEPEPIRDGMLLTLP
EGFGFEIELAPSRALDAQAYPSGGAGMVGDADDVLQLVETLRTGKEGILQPATAALMRQA
HVGSHAETQGPGWGFGFGGAVLEDAQLAATPQHNGTLQWGGVYGHSWFYDPQAAISVVAL
TNTAFEGMSGRYPLQIRDAVYGTNEPTR

Figure 5

ATGACCGATCCCTATGTGCGCCCCGATGTGGCGATGTTTCTGGCTTTCCTTAACAATGCGCCG
GGACCAAAGCTGCACGAATTAAGCGCGCCCGAAGCGCGGATGGTGCAAAATGCCATGCGCGAC
ATGGCCGACGCGCCGGTTGGTGAGCTTGCCGTTATGCGCGATCTGGAAATTCCGGGGCCAGCC
GGAACCATAATGGCGCGGCTTTACGATAAGCAGCCGGGGCGAGGCTCTGGTCCGGCGATGGTA
TTCTTCCACGGTGGCGGGTTCGTTATCGGCAACATCCATACGTACGAACCCTTTTGCGCCGAG
GTCGCGCGCCTACTCGACCTTCCAGTCATTTCGGTCGAATACCGGCTTGGGCCGGAATCTCCA
TTCCCCGCCGCCTTCGAGGATTGCGAAGCTGCGGCGCGCTGGGTAGCCAGCAAGCCCGAAGCA
TTGGGCTTTGATGTTTCCGGCCTCATCCTGTCGGGCGACAGTGCAGGCGGCAACCTCACCATT
TCGACAAGCATGGCGTTGCGCGACGTTGCAGCCGGGGTGCCAGTAATCGCCCAAATGCCGATC
TATCCGGTGGTGACACTCGATCCGGACTGGCCCAGCATGCGCGACTTTGCCGACGGCTATTTA
CTCACTGCCGAGCTCATTCAATGGTTCGGCGACGGGCATGGCGCAAGCGGCGAGGATTATCGG
ACGCATCCGCTCGACTTCGACCAGTCGGGAATGCCGCCAACGGTGATTACCACGGCAAGCCTC
GATCCGCTGCGCGATCAGGGCATGGCCTATTTCGAAAAGCTCAAAGCCGCTGGAGTCCGCGCC
GAACATATCAGCGCCGAGGGTAATATCCACGGCCATATCAATGTACGCAAAGGCATTCCGTCG
AGCCAGCAGGATGTAGAAGGTTATGTTACCGCGCTAACGGCGATGCTGGCCGGGGTTATGGCA
GAAGCATGA

Figure 6

MTDPYVRPDVAMFLAFLNNAPGPKLHELSAPEARMVQNAMRDMADAPVGELAVMRDLEIPGPA
GTIMARLYDKQPGRGSGPAMVFFHGGGFVIGNIHTYEPFCAEVARLLDLPVISVEYRLGPESP
FPAAFEDCEAAARWVASKPEALGFDVSGLILSGDSAGGNLTISTSMALRDVAAGVPVIAQMPI
YPVVTLDPDWPSMRDFADGYLLTAELIQWFGDGHGASGEDYRTHPLDFDQSGMPPTVITTASL
DPLRDQGMAYFEKLKAAGVRAEHISAEGNIHGHINVRKGIPSSQQDVEGYVTALTAMLAGVMA
EA

Figure 7

ATGAAAAGAAAAACAATCTTCTCCCGTTTGTCGTTTGCTGCTTTGGGATTGTTTGCTGTCGCG
ACGATTGCGCTGGATGCAAAGGCGGCAACCACCTGTCCTGCAGGCGCTATCTGCCGTTATGAA
GAGGCGCCGGGCTCATACAGCGGCAACGGCCCCTATACGGTGAGAAGTTACACGCTGTCCAGA
TTGCAGACGCCGGGCGGCGCTACCGTTTATTACCCGTCCAATGCCAGGCCGCCATTCTCGGGC
GTCGTTTTCACTCCCCCCTATACCGGCATCCAGTCCATGTTTGCAGCCTGGGGCCCTTTCTTT
GCGTCGCACGGTATTGTGATGGTGACCATGGATACCAACACCACGCTGGACACGGTGGACCAG
CGCGCGAGCCAGCAGAAGCAGGTACTGGATGCGCTGAAAAGGGAAAATACCCGCTCCGCCAGT
GCGTTGTATGGCAAGCTGAATACGGCGCGCCTGGGTGCGGTGGGCTGGTCGATGGGTGGCGGC
GCCACTTGGATCAACTCTGCTGAATATGCCGGACTGAAGAGCGCCATGTCGCTGGCGGGACAC
AATCTGACAACGGTGGATATCGATTCCAGAGGTGGCAACACACGCATTCCCACCCTGATTCTG
AATGGCGCGCTTGATCTCACCTATCTGGGTGGGTTGGGCCAGTCCGATGGCGTCTACAATAAT
ATTCGCAGTGGTGTGCCCAAGGTGTTTTATGAAGTGTCGAGCGCGGGCCATTTCGCCTGGGGT
TCTCCGACATCAGCCAATCGGGCGGTTGCCGGCATTGCGCTGGCGTTCCACAAGACTTTTCTG
GATGGTGACACGCGCTGGGTGAGTTACATCAAGCGCCCAGCTCTGATGTGTCCAAGTGGGCG
ACTGCAAGTTTGCCGCAGTAA

Figure 8

MKRKTIFSRLSFAALGLFAVATIALDAKAATTCPAGAICRYEEAPGSYSGNGPYTVRSYTLSR
LQTPGGATVYYPSNARPPFSGVVFTPPYTGIQSMFAAWGPFFASHGIVMVTMDTNTTLDTVDQ
RASQQKQVLDALKRENTRSASALYGKLNTARLGAVGWSMGGGATWINSAEYAGLKSAMSLAGH
NLTTVDIDSRGGNTRIPTLILNGALDLTYLGGLGQSDGVYNNIRSGVPKVFYEVSSAGHFAWG
SPTSANRAVAGIALAFHKTFLDGDTRWVSYIKRPSSDVSKWATASLPQ total conversion

Figure 10
Seq ID No. 2
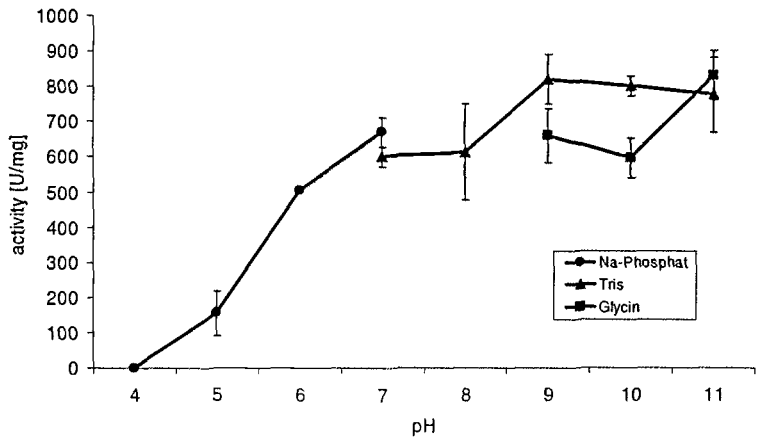
Seq ID No. 4
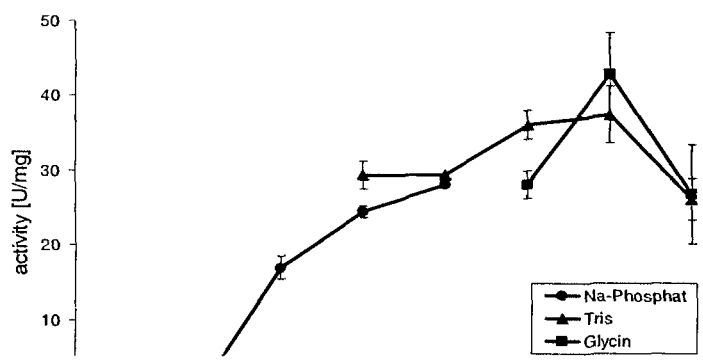
Seq ID No. 6
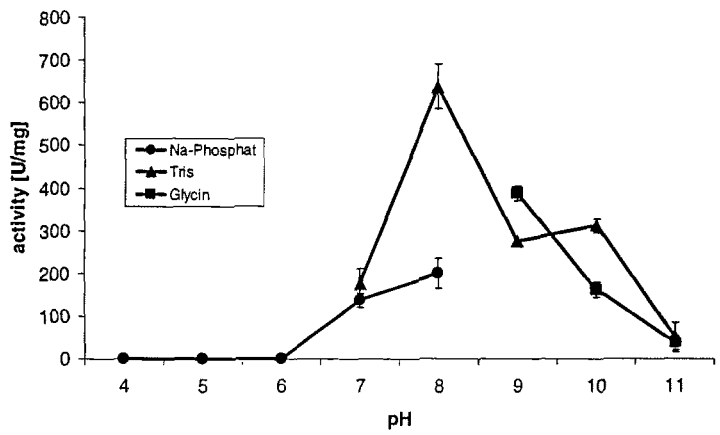

Figure 11
Seq ID No. 2
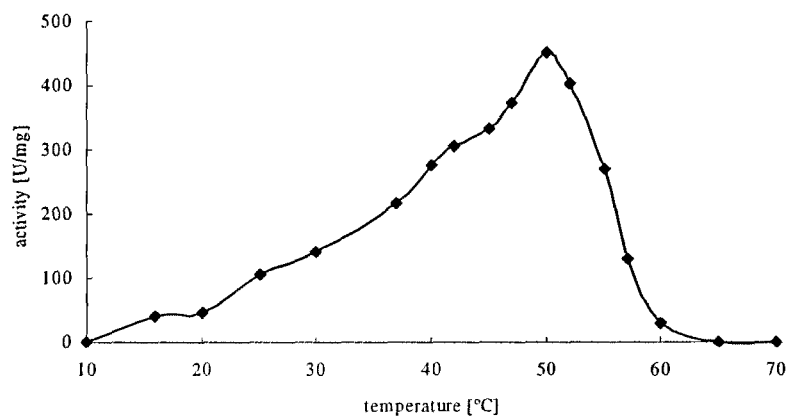
Seq ID No. 4
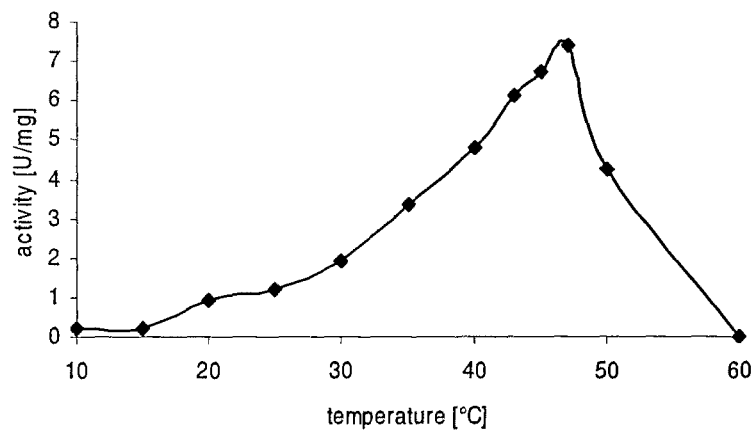

Figure 12
Seq ID No. 4
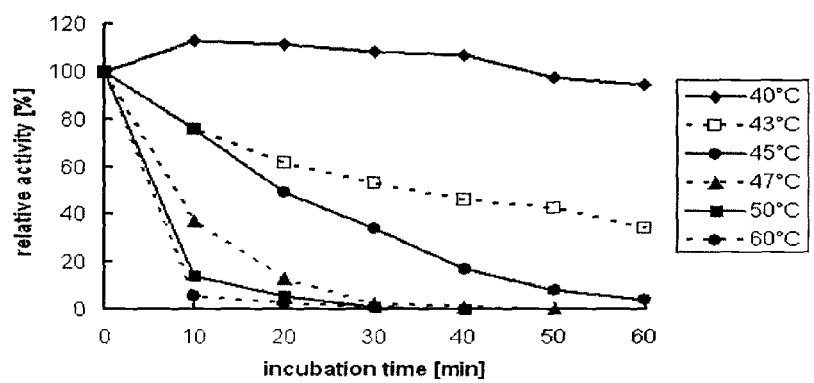
Seq ID No. 2
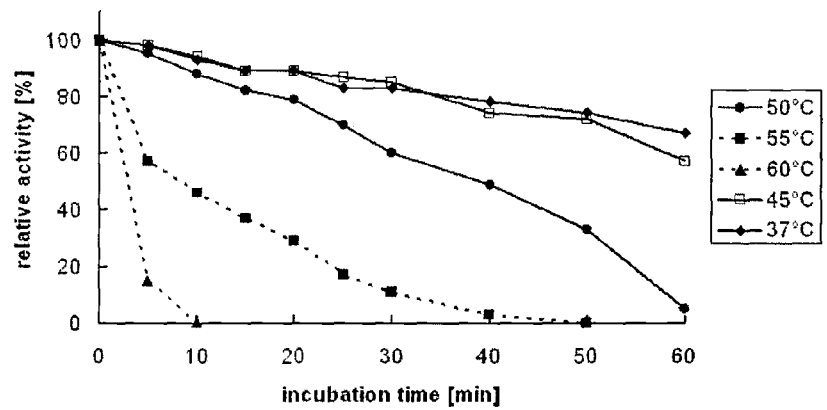

SEQUENCE LISTING

<160> NUMBER OF SEQ ID NOS: 22

<210> SEQ ID NO 1
<211> LENGTH: 1191
<212> TYPE: DNA
<213> ORGANISM: unknown
<220> FEATURE:
<223> OTHER INFORMATION: metagenomic sequence

<400> SEQUENCE: 1

```
atgagcgccg aagaactagg gttcctgccc gaccgcctag cgcggatcag cgatcatatc      60
cagaccaact atctcgacaa tggcaagctg ccttttgcgt cgctgctgat cggtcgcggc     120
gacgacatcg ccctgcaatg gagttcgggc gtcgccgacg atgctatttt ccgcattgca     180
tcgatgacca aaccggtcac ctcggttgcg ttcatgcaac tggtcgaaca gggcaaagtc     240
gccctgaccg acccggtcgc caagtatatc cccgaatttg ccaagctcgg cgttttcgtt     300
gccggcggcg gcaatatacc ctttgtcagt cgcccgccga caatgccgat gcggattgtc     360
gatgtgttgc ggcacacaac gggttttacc tatagctttc aggaacgaag caacatcgac     420
gcggcctacc ggaagaccga tgtcgagagc tggacaagaa gcacgtcaca gagcttcatc     480
gacacgctgg ctgaaatccc gctcgagttc gaccctggca cgcagtggaa ttattcggtt     540
tcgaccgatg tattgggcat attgatcgag cgaatcagcg ggcaatcgct tcctgactat     600
ttccgcgacc atatcttcgc gccgctcggg atggtcgaca cgtgctttac cgttcccgcc     660
gacaaggcag cgcgaatccc gcaatgcttt gccttcgacc cggcaaccaa aatgaaattg     720
```

```
ttcgatgaag ctggcgcaag tagcctgtgg accaaaggct ggtcgttcaa ttcaggcgga     780
ggcgggctgg cttcgagcgt cgcggattat caccggttct gccggatgct gctgaacggc     840
ggcgcacttg acggtatcca gatcatcagc ccgaaaacac tcgaactgat gaccgccaac     900
catttaccgg gcgggcaaga cctcacgcaa atgtcgaaat ccttgttcag cgaggccgaa     960
atggcgggca tcggctttgg cctgggtttt gccaccacga tcgatagcgt agcgacgctc    1020
accccatgct ctacgggcga ttttactggg ggcggcatgt attcgaccgc gttcttcgtc    1080
gatccggtcg aggatatcat catgatcttt atgactcaat tgatgccgtc gagcacctat    1140
ccggtgcggc gcgaaatcaa gacgatgatc tacagcgcgc tcgccgccta a             1191
```

<210> SEQ ID NO 2
<211> LENGTH: 396
<212> TYPE: PRT
<213> ORGANISM: unknown
<220> FEATURE:
<223> OTHER INFORMATION: metagenomic sequence

<400> SEQUENCE: 2

```
Met Ser Ala Glu Glu Leu Gly Phe Leu Pro Asp Arg Leu Ala Arg Ile
1               5                   10                  15

Ser Asp His Ile Gln Thr Asn Tyr Leu Asp Asn Gly Lys Leu Pro Phe
            20                  25                  30

Ala Ser Leu Leu Ile Gly Arg Gly Asp Asp Ile Ala Leu Gln Trp Ser
        35                  40                  45

Ser Gly Val Ala Asp Asp Ala Ile Phe Arg Ile Ala Ser Met Thr Lys
    50                  55                  60

Pro Val Thr Ser Val Ala Phe Met Gln Leu Val Glu Gln Gly Lys Val
65                  70                  75                  80

Ala Leu Thr Asp Pro Val Ala Lys Tyr Ile Pro Glu Phe Ala Lys Leu
                85                  90                  95

Gly Val Phe Val Ala Gly Gly Asn Ile Pro Phe Val Ser Arg Pro
            100                 105                 110

Pro Thr Met Pro Met Arg Ile Val Asp Val Leu Arg His Thr Thr Gly
        115                 120                 125

Phe Thr Tyr Ser Phe Gln Glu Arg Ser Asn Ile Asp Ala Ala Tyr Arg
    130                 135                 140

Lys Thr Asp Val Glu Ser Trp Thr Arg Ser Thr Ser Gln Ser Phe Ile
145                 150                 155                 160

Asp Thr Leu Ala Glu Ile Pro Leu Glu Phe Asp Pro Gly Thr Gln Trp
                165                 170                 175

Asn Tyr Ser Val Ser Thr Asp Val Leu Gly Ile Leu Ile Glu Arg Ile
            180                 185                 190

Ser Gly Gln Ser Leu Pro Asp Tyr Phe Arg Asp His Ile Phe Ala Pro
        195                 200                 205

Leu Gly Met Val Asp Thr Cys Phe Thr Val Pro Ala Asp Lys Ala Ala
    210                 215                 220

Arg Ile Pro Gln Cys Phe Ala Phe Asp Pro Ala Thr Lys Met Lys Leu
225                 230                 235                 240

Phe Asp Glu Ala Gly Ala Ser Ser Leu Trp Thr Lys Gly Trp Ser Phe
                245                 250                 255

Asn Ser Gly Gly Gly Gly Leu Ala Ser Ser Val Ala Asp Tyr His Arg
            260                 265                 270

Phe Cys Arg Met Leu Leu Asn Gly Gly Ala Leu Asp Gly Ile Gln Ile
        275                 280                 285
```

```
Ile Ser Pro Lys Thr Leu Glu Leu Met Thr Ala Asn His Leu Pro Gly
    290                 295                 300
Gly Gln Asp Leu Thr Gln Met Ser Lys Ser Leu Phe Ser Glu Ala Glu
305                 310                 315                 320
Met Ala Gly Ile Gly Phe Gly Leu Gly Phe Ala Thr Thr Ile Asp Ser
                325                 330                 335
Val Ala Thr Leu Thr Pro Cys Ser Thr Gly Asp Phe Tyr Trp Gly Gly
            340                 345                 350
Met Tyr Ser Thr Ala Phe Phe Val Asp Pro Val Glu Asp Ile Ile Met
        355                 360                 365
Ile Phe Met Thr Gln Leu Met Pro Ser Ser Thr Tyr Pro Val Arg Arg
    370                 375                 380
Glu Ile Lys Thr Met Ile Tyr Ser Ala Leu Ala Ala
385                 390                 395
```

<210> SEQ ID NO 3
<211> LENGTH: 1167
<212> TYPE: DNA
<213> ORGANISM: unknown
<220> FEATURE:
<223> OTHER INFORMATION: metagenomic sequence

<400> SEQUENCE: 3

```
atgtcgatag cggatcagtc attagcaaaa agagtgcagg gcgttagcca acaggcgatt      60
gatgaagggc gtatcgttgg cagcgtggtg ctgatcgctc ggcacggtcg cgtgatttac     120
gccaatgcca gcggctatgc cgatcgtgaa cagaagaaac ctatggtgcg tgagacccaa     180
tttcggctgt cgtcggtgtc caagccttat attacgctgg cggccatgcg tatgatcgaa     240
cagcagaagc tggggctgga tgataccgtc agccgttggt tgccgtggtt taccccggcg     300
ctggccgatg gggttcgccc gccaattaaa atccgtcact tgttgagcca cactgccggc     360
ctggattatc gtttgagcca acctgcggaa ggaccgtatc atcgactcgg tattaaagac     420
ggtatggaac tgtcgtcgtt aacgctggaa cagaatctgc gcctgttggc gcaggcggat     480
ctgttggccg agccgggcag cgagtttcga tattcactgg caatcgatgt gctggggggcg     540
gtgctggaac aggtggcggg cgagcccttg ccgcaggtgt caaccattgg gttgcccaa      600
cctttggggt tgcgtaatac cggtttttac accaccgatg tcgataatct ggcaacggcg     660
tatcacgaca ccgccgcgga gccggaacct atacgagatg gcatgttgct gaccctgccg     720
gaagggttcg gcttcgagat tgaactggca ccctcgcgcg cactggacgc tcaggcctat     780
ccttctggcg gcgctggcat ggtcggcgat gcagacgatg tgttgcagtt ggtggaaacc     840
ttgcgcactg gcaaggaagg cattttacag ccggccaccg cagcgctgat gcgtcaagcg     900
catgtcgggt cgcacgccga gactcagggg cccggctggg ggtttggttt cggcggtgcg     960
gtactggaag atgcgcagtt ggcggcgacg cctcagcaca atggcactct gcagtggggc    1020
ggtgtctatg gccacagttg gttttacgat ccgcaagcgg cgatcagcgt ggtagccttg    1080
accaatacgg cctttgaagg catgagtgga cgttatccac tgcaaatccg cgatgctgtt    1140
tacgggacaa acgaacctac tcgctaa                                        1167
```

<210> SEQ ID NO 4
<211> LENGTH: 388
<212> TYPE: PRT
<213> ORGANISM: unknown
<220> FEATURE:
<223> OTHER INFORMATION: metagenomic sequence -continued

```
<400> SEQUENCE: 4

Met Ser Ile Ala Asp Gln Ser Leu Ala Lys Arg Val Gln Gly Val Ser
1               5                   10                  15

Gln Gln Ala Ile Asp Glu Gly Arg Ile Val Gly Ser Val Val Leu Ile
            20                  25                  30

Ala Arg His Gly Arg Val Ile Tyr Ala Asn Ala Ser Gly Tyr Ala Asp
        35                  40                  45

Arg Glu Gln Lys Lys Pro Met Val Arg Glu Thr Gln Phe Arg Leu Ser
    50                  55                  60

Ser Val Ser Lys Pro Tyr Ile Thr Leu Ala Ala Met Arg Met Ile Glu
65                  70                  75                  80

Gln Gln Lys Leu Gly Leu Asp Asp Thr Val Ser Arg Trp Leu Pro Trp
                85                  90                  95

Phe Thr Pro Ala Leu Ala Asp Gly Val Arg Pro Ile Lys Ile Arg
            100                 105                 110

His Leu Leu Ser His Thr Ala Gly Leu Asp Tyr Arg Leu Ser Gln Pro
            115                 120                 125

Ala Glu Gly Pro Tyr His Arg Leu Gly Ile Lys Asp Gly Met Glu Leu
        130                 135                 140

Ser Ser Leu Thr Leu Glu Gln Asn Leu Arg Leu Leu Ala Gln Ala Asp
145                 150                 155                 160

Leu Leu Ala Glu Pro Gly Ser Glu Phe Arg Tyr Ser Leu Ala Ile Asp
                165                 170                 175

Val Leu Gly Ala Val Leu Glu Gln Val Ala Gly Glu Pro Leu Pro Gln
            180                 185                 190

Val Phe Asn His Trp Val Ala Gln Pro Leu Gly Leu Arg Asn Thr Gly
        195                 200                 205

Phe Tyr Thr Thr Asp Val Asp Asn Leu Ala Thr Ala Tyr His Asp Thr
    210                 215                 220

Ala Ala Glu Pro Glu Pro Ile Arg Asp Gly Met Leu Leu Thr Leu Pro
225                 230                 235                 240

Glu Gly Phe Gly Phe Glu Ile Glu Leu Ala Pro Ser Arg Ala Leu Asp
                245                 250                 255

Ala Gln Ala Tyr Pro Ser Gly Gly Ala Gly Met Val Gly Asp Ala Asp
            260                 265                 270

Asp Val Leu Gln Leu Val Glu Thr Leu Arg Thr Gly Lys Glu Gly Ile
        275                 280                 285

Leu Gln Pro Ala Thr Ala Ala Leu Met Arg Gln Ala His Val Gly Ser
    290                 295                 300

His Ala Glu Thr Gln Gly Pro Gly Trp Gly Phe Gly Phe Gly Ala
305                 310                 315                 320

Val Leu Glu Asp Ala Gln Leu Ala Thr Pro Gln His Asn Gly Thr
                325                 330                 335

Leu Gln Trp Gly Gly Val Tyr Gly His Ser Trp Phe Tyr Asp Pro Gln
            340                 345                 350

Ala Ala Ile Ser Val Val Ala Leu Thr Asn Thr Ala Phe Glu Gly Met
        355                 360                 365

Ser Gly Arg Tyr Pro Leu Gln Ile Arg Asp Ala Val Tyr Gly Thr Asn
    370                 375                 380

Glu Pro Thr Arg
385
```

<210> SEQ ID NO 5
<211> LENGTH: 954
<212> TYPE: DNA
<213> ORGANISM: unknown
<220> FEATURE:
<223> OTHER INFORMATION: metagenomic sequence

<400> SEQUENCE: 5

```
atgaccgatc cctatgtgcg ccccgatgtg gcgatgtttc tggctttcct taacaatgcg      60
ccgggaccaa agctgcacga attaagcgcg cccgaagcgc ggatggtgca aaatgccatg     120
cgcgacatgg ccgacgcgcc ggttggtgag cttgccgtta tgcgcgatct ggaaattccg     180
gggccagccg gaaccataat ggcgcggctt tacgataagc agccggggcg aggctctggt     240
ccggcgatgg tattcttcca cggtggcggg ttcgttatcg gcaacatcca tacgtacgaa     300
cccttttgcg ccgaggtcgc gcgcctactc gaccttccag tcatttcggt cgaataccgg     360
cttgggccgg aatctccatt ccccgccgcc ttcgaggatt gcgaagctgc ggcgcgctgg     420
gtagccagca agcccgaagc attgggcttt gatgtttccg gcctcatcct gtcgggcgac     480
agtgcaggcg gcaacctcac catttcgaca agcatggcgt tgcgcgacgt tgcagccggg     540
gtgccagtaa tcgcccaaat gccgatctat ccggtggtga cactcgatcc ggactggccc     600
agcatgcgcg actttgccga cggctattta ctcactgccg agctcattca atggttcggc     660
gacgggcatg gcgcaagcgg cgaggattat cggacgcatc cgctcgactt cgaccagtcg     720
ggaatgccgc caacggtgat taccacggca agcctcgatc cgctgcgcga tcagggcatg     780
gcctatttcg aaaagctcaa agccgctgga gtccgcgccg aacatatcag cgccgagggt     840
aatatccacg ccatatcaa tgtacgcaaa ggcattccgt cgagccagca ggatgtagaa     900
ggttatgtta ccgcgctaac ggcgatgctg gccggggtta tggcagaagc atga          954
```

<210> SEQ ID NO 6
<211> LENGTH: 317
<212> TYPE: PRT
<213> ORGANISM: unknown
<220> FEATURE:
<223> OTHER INFORMATION: metagenomic sequence

<400> SEQUENCE: 6

Met Thr Asp Pro Tyr Val Arg Pro Asp Val Ala Met Phe Leu Ala Phe
1               5                   10                  15

Leu Asn Asn Ala Pro Gly Pro Lys Leu His Glu Leu Ser Ala Pro Glu
            20                  25                  30

Ala Arg Met Val Gln Asn Ala Met Arg Asp Met Ala Asp Ala Pro Val
        35                  40                  45

Gly Glu Leu Ala Val Met Arg Asp Leu Glu Ile Pro Gly Pro Ala Gly
    50                  55                  60

Thr Ile Met Ala Arg Leu Tyr Asp Lys Gln Pro Gly Arg Gly Ser Gly
65                  70                  75                  80

Pro Ala Met Val Phe Phe His Gly Gly Gly Phe Val Ile Gly Asn Ile
                85                  90                  95

His Thr Tyr Glu Pro Phe Cys Ala Glu Val Ala Arg Leu Leu Asp Leu
            100                 105                 110

Pro Val Ile Ser Val Glu Tyr Arg Leu Gly Pro Glu Ser Pro Phe Pro
        115                 120                 125

Ala Ala Phe Glu Asp Cys Glu Ala Ala Arg Trp Val Ala Ser Lys
    130                 135                 140

Pro Glu Ala Leu Gly Phe Asp Val Ser Gly Leu Ile Leu Ser Gly Asp

```
                145                 150                 155                 160
Ser Ala Gly Gly Asn Leu Thr Ile Ser Thr Ser Met Ala Leu Arg Asp
                    165                 170                 175

Val Ala Ala Gly Val Pro Val Ile Ala Gln Met Pro Ile Tyr Pro Val
                    180                 185                 190

Val Thr Leu Asp Pro Asp Trp Pro Ser Met Arg Asp Phe Ala Asp Gly
                    195                 200                 205

Tyr Leu Leu Thr Ala Glu Leu Ile Gln Trp Phe Gly Asp Gly His Gly
                    210                 215                 220

Ala Ser Gly Glu Asp Tyr Arg Thr His Pro Leu Asp Phe Asp Gln Ser
225                 230                 235                 240

Gly Met Pro Pro Thr Val Ile Thr Thr Ala Ser Leu Asp Pro Leu Arg
                    245                 250                 255

Asp Gln Gly Met Ala Tyr Phe Glu Lys Leu Lys Ala Ala Gly Val Arg
                    260                 265                 270

Ala Glu His Ile Ser Ala Glu Gly Asn Ile His Gly His Ile Asn Val
                    275                 280                 285

Arg Lys Gly Ile Pro Ser Ser Gln Gln Asp Val Glu Gly Tyr Val Thr
                    290                 295                 300

Ala Leu Thr Ala Met Leu Ala Gly Val Met Ala Glu Ala
305                 310                 315

<210> SEQ ID NO 7
<211> LENGTH: 903
<212> TYPE: DNA
<213> ORGANISM: unknown
<220> FEATURE:
<223> OTHER INFORMATION: metagenomic sequence

<400> SEQUENCE: 7
atgaaaagaa aaacaatctt ctcccgtttg tcgtttgctg ctttgggatt gtttgctgtc    60
gcgacgattg cgctggatgc aaaggcggca accacctgtc ctgcaggcgc tatctgccgt   120
tatgaagagg cgccgggctc atacagcggc aacggcccct atacggtgag aagttacacg   180
ctgtccagat tgcagacgcc gggcggcgct accgtttatt acccgtccaa tgccaggccg   240
ccattctcgg gcgtcgtttt cactcccccc ataccggca tccagtccat gtttgcagcc   300 tggggcccctt tctttgcgtc gcacggtatt gtgatggtga ccatggatac caacaccacg   360
ctggacacgg tggaccagcg cgcgagccag cagaagcagg tactggatgc gctgaaaagg   420
gaaaataccc gctccgccag tgcgttgtat ggcaagctga atacgcgcg cctgggtgcg   480 gtgggctggt cgatgggtgg cggcgccact tggatcaact ctgctgaata tgccggactg   540
aagagcgcca tgtcgctggc gggacacaat ctgacaacgg tggatatcga ttccagaggt   600
ggcaacacac gcattcccac cctgattctg aatggcgcgc ttgatctcac ctatctgggt   660
gggttgggcc agtccgatgg cgtctacaat aatattcgca gtggtgtgcc caaggtgttt   720
tatgaagtgt cgagcgcggg ccatttcgcc tggggttctc cgacatcagc caatcgggcg   780
gttgccggca ttgcgctggc gttccacaag acttttctgg atggtgacac gcgctgggtg   840
agttacatca agcgccccag ctctgatgtg tccaagtggg cgactgcaag tttgccgcag   900
taa                                                                 903

<210> SEQ ID NO 8
<211> LENGTH: 300
<212> TYPE: PRT
<213> ORGANISM: unknown
```

<220> FEATURE:
<223> OTHER INFORMATION: metagenomic sequence

<400> SEQUENCE: 8

Met Lys Arg Lys Thr Ile Phe Ser Arg Leu Ser Phe Ala Ala Leu Gly
1               5                   10                  15

Leu Phe Ala Val Ala Thr Ile Ala Leu Asp Ala Lys Ala Ala Thr Thr
            20                  25                  30

Cys Pro Ala Gly Ala Ile Cys Arg Tyr Glu Glu Ala Pro Gly Ser Tyr
        35                  40                  45

Ser Gly Asn Gly Pro Tyr Thr Val Arg Ser Tyr Thr Leu Ser Arg Leu
    50                  55                  60

Gln Thr Pro Gly Gly Ala Thr Val Tyr Tyr Pro Ser Asn Ala Arg Pro
65                  70                  75                  80

Pro Phe Ser Gly Val Val Phe Thr Pro Pro Tyr Thr Gly Ile Gln Ser
                85                  90                  95

Met Phe Ala Ala Trp Gly Pro Phe Phe Ala Ser His Gly Ile Val Met
            100                 105                 110

Val Thr Met Asp Thr Asn Thr Thr Leu Asp Thr Val Asp Gln Arg Ala
        115                 120                 125

Ser Gln Gln Lys Gln Val Leu Asp Ala Leu Lys Arg Glu Asn Thr Arg
    130                 135                 140

Ser Ala Ser Ala Leu Tyr Gly Lys Leu Asn Thr Ala Arg Leu Gly Ala
145                 150                 155                 160

Val Gly Trp Ser Met Gly Gly Ala Thr Trp Ile Asn Ser Ala Glu
                165                 170                 175

Tyr Ala Gly Leu Lys Ser Ala Met Ser Leu Ala Gly His Asn Leu Thr
            180                 185                 190

Thr Val Asp Ile Asp Ser Arg Gly Gly Asn Thr Arg Ile Pro Thr Leu
        195                 200                 205

Ile Leu Asn Gly Ala Leu Asp Leu Thr Tyr Leu Gly Gly Leu Gly Gln
    210                 215                 220

Ser Asp Gly Val Tyr Asn Asn Ile Arg Ser Gly Val Pro Lys Val Phe
225                 230                 235                 240

Tyr Glu Val Ser Ser Ala Gly His Phe Ala Trp Gly Ser Pro Thr Ser
                245                 250                 255

Ala Asn Arg Ala Val Ala Gly Ile Ala Leu Ala Phe His Lys Thr Phe
            260                 265                 270

Leu Asp Gly Asp Thr Arg Trp Val Ser Tyr Ile Lys Arg Pro Ser Ser
        275                 280                 285

Asp Val Ser Lys Trp Ala Thr Ala Ser Leu Pro Gln
    290                 295                 300

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Forward
      Primer

<400> SEQUENCE: 9
ggcatatgtc gatagcggat cagtca                                          26

<210> SEQ ID NO 10
<211> LENGTH: 26
<212> TYPE: DNA

```
<213> ORGANISM: Artificial Sequence
<220> FEATURE:
<223> OTHER INFORMATION: Description of Artificial Sequence: Reverse
      Primer

<400> SEQUENCE: 10
ggatccttag cgagtaggtt cgtttg                                          26

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 11
gcggatccat gagcgccgaa gaactaggg                                       29

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Forward
      Primer

<400> SEQUENCE: 12
cgaagcttgg cggcgagcgc gctgta                                          26

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Reverse
      Primer

<400> SEQUENCE: 13
agagaccata tgaccgatcc ctatgtgcg                                       29

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 14
cggtttggat cctcatgctt ctgccataac                                      30

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 15
actatccata tgaaagaaa aacaatcttc                                       30

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: Primer
```

```
<400> SEQUENCE: 16
ttagttaagc ttctgcggca aacttgcag                                           29

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Consensus
      motif
<220> FEATURE:
<221> NAME/KEY: misc_feature
<222> LOCATION: (1)..(1)
<223> OTHER INFORMATION: Xaa is a small amino acid
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 17

Xaa Xaa Ser Xaa Gly
1               5

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Consensus
      motif
<220> FEATURE:
<221> NAME/KEY: misc_feature
<222> LOCATION: (4)..(4)
<223> OTHER INFORMATION: Xaa can be any naturally occurring amino acid

<400> SEQUENCE: 18

Gly Gly Gly Xaa
1

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Consensus
      motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 19

Gly Xaa Ser Xaa Gly Gly
1               5

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Consensus
      motif
<220> FEATURE:
```

```
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 20

Pro Thr Xaa Xaa Xaa Xaa Gly Xaa Xaa Asp
1               5                   10

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Consensus
      motif
<220> FEATURE:
<221> NAME/KEY: misc_feature
<222> LOCATION: (2)..(3)
<223> OTHER INFORMATION: Xaa can be any naturally occurring amino acid

<400> SEQUENCE: 21

Ser Xaa Xaa Lys
1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Consensus
      motif

<400> SEQUENCE: 22

Gly Asp Ser Leu
1
```

CARBOXYL ESTERASE POLYPEPTIDES

This application is the National Phase of International Application PCT/EP2007/003772 filed Apr. 27, 2007 which designated the U.S. and that International Application.

The present invention relates to a polynucleotide encoding an enzyme having carboxyl esterase [E.C. 3.1.1.1] activity, wherein the coding sequence is selected from the group consisting of (a) a polynucleotide encoding an amino acid sequence as depicted in any one of SEQ ID NOs: 2, 4, 6 and 8; (b) a polynucleotide having or comprising a nucleotide sequence encoding an enzyme, wherein the nucleic acid sequence is as shown in any one of SEQ ID NOs: 1, 3, 5 and 7; (c) a polynucleotide having or comprising a nucleotide sequence encoding a fragment or derivative of an enzyme encoded by a polynucleotide of (a) or (b), wherein in said derivative one or more amino acid residues are conservatively substituted compared to the amino acid sequence of (a); (d) a polynucleotide encoding an enzyme having carboxyl esterase activity which polynucleotide is at least 65% identical to a polynucleotide encoding an enzyme as shown in one of SEQ ID NOs: 2, 4, 6 and 8; (e) a polynucleotide having or comprising a nucleotide sequence the complementary strand of which hybridizes to a polynucleotide as defined in any one of (a) to (d); and (f) a polynucleotide having or comprising a nucleotide sequence being degenerate to the nucleotide sequence of the polynucleotide of (d) or (e); or the complementary strand of such a polynucleotide of (a) to (f) or fragments thereof useful as specific probes or primers. The present invention also relates to a host, genetically engineered with the polynucleotide of the present invention or the vector of the present invention. The present invention also relates to a polypeptide comprising the amino acid sequence encoded by a polynucleotide of the present invention or which is obtainable by the process of the present invention. Moreover, the present invention relates to a process for producing said polypeptide and for producing bacteria expressing said polypeptide. Finally, the present invention relates to a composition comprising the polynucleotide of the present invention, the vector of the present invention, the host of the present invention, the polypeptide of the present invention, the antibody of the present invention and/or one or more primers of the present invention.

Several documents are cited throughout the text of this specification. The disclosure content of the documents cited herein (including any manufacturer's specifications, instructions, etc.) is herewith incorporated by reference.

The use of enzymes as biocatalyst in the chemical industry has markedly increased during the last 20 years [1]. Breakthroughs in the key biotechnological areas of a) genetic resource access b) enzyme screening and discovery and c) in vitro evolution of proteins to find and optimize enzymes to become near-ideally suited biocatalysts have been instrumental in pushing industrial biocatalysis to where it stands today [2]. However, the feasibility of new biocatalytic processes will often be determined by the availability of the appropriate biocatalyst [3].

Application of modern screening technology to biodiversity—nature's plethora of individual solutions to billion years of stringent selection for superior performance in ecological niches structured by a multitude of biophysical and biochemical pressures, is clearly a rewarding approach to find industrially relevant enzymes. Screening cultivable microorganisms is a powerful and still the most common way for obtaining biocatalysts. However cultivation is limited as most microorganisms cannot be cultivated using current technologies [2].

The development of techniques to directly extract, clone and recombinantly express genomic DNA from entire uncultured microbial consortia, the so called "metagenome" approach, allows to access the "unseen" majority of microbial diversity and its enzymatic constituents. Basically microbial cells are lysed either still in the context of natural substrates or after physical separation to yield high molecular weight DNA. This DNA has to be purified from co-extracted inhibitors prior to proceeding with standard cloning procedures. Finally the metagenomic DNA ends up being propagated and possibly expressed in cultivable surrogate hosts like E. coli to be subjected to screening or selection procedures [2].

Carboxylesterases [EC 3.1.1.1] and lipases [EC 3.1.1.3] represent a diverse group of hydrolytic enzymes catalysing the cleavage and formation of ester bonds. The discrimination of esterases and lipases is usually based on the acyl chain length of their ester substrates: while esterases hydrolyse preferentially short chain water-soluble ester substrates, lipases are capable of hydrolysing also water insoluble, emulsified long chain ester substrates.

Many esterases and lipases share the same characteristic α/β hydrolase fold [4], a three-dimensional structure composed of a central, mostly parallel β-sheet shielded against the solvent by α-helices. However, the primary structures of these proteins are very often rather different showing identity levels sometimes <30%. The catalytic triad is composed of Ser-Asp-His (Glu instead of Asp for some enzymes) and usually also a consensus sequence (Sm-x-Ser-x-Gly) (SEQ ID NO:17) is found around the active site serine where "Sm" is a small amino acid (usually a glycine) and "x" is any amino acid. Besides the catalytic triad the so called oxyanion hole is essential for the enzymatic activity. Its function is to stabilize the oxyanions of the carboxylic acid oxygen of the tetrahedral intermediates formed during the catalytic process.

More recently, esterases have been identified containing a "GDSL" (SEQ ID NO:22) -amino acid motif around the active site serine as well as enzymes showing high homology to class C β-lactamases [5]. Based on the analysis of their amino acid sequence, Arpigny and Jaeger [6] suggested a classification for bacterial esterases and lipases which identified 8 families and 6 subfamilies.

Esterase family IV is characterised not only by the conserved catalytic triad and the consensus sequence around the active site serine but also by a highly conserved "GGGX"-motif (SEQ ID NO:18) comprising part of the oxyanion hole [6]). This structural motif (GGGX) distinguishes family IV from all other esterases showing an α/β hydrolase fold and led to the classification of esterases in "GGGX"-type and "GX"-type esterases [7]. It was found that the presence of the GGGX-type motif correlates with the capability of these enzymes to hydrolyse the esters of tertiary alcohols (TAE) [8]. Tertiary alcohols (TA) and TAEs represent a very important group of molecules and constitute very useful synthons for the production of fine chemicals [9]. They are found in several natural products, e.g. α-terpineol and linalool, which is an important terpene alcohol of the flavour and fragrance industry. The two different stereoisomers of linalool, licareol (the R-(−) enantiomer) and coriandrol (the S-(+) enantiomer), differ in their fragrance so that it is desirable to separate the optically pure isomers for the production of flavour and fragrance compositions.

Esterase family V comprises enzymes which share significant similarity to various bacterial non-lipolytic enzymes, namely epoxide hydrolases, dehalogenases, haloperoxidases and other α/β hydrolases [6]. Furthermore, the members of this family are characterized by the sequence motif "Gly-X-Ser-X-Gly-Gly" (SEQ ID NO:19) around the active site serine and the motif "Pro-Thr-X$_4$-Gly-X$_2$-Asp"(SEQ ID NO:20) preceeding the active site aspartate.

Family VIII comprises enzymes which show higher homology to class C β-lactamases than to other esterases. This family is characterised by the active site motif "Ser-x-x-Lys"(SEQ ID NO:21) which is typical for class C β-lactamases. Enzymes belonging to this esterase-family usually do not hydrolyse β-lactams. Furthermore, although these proteins also form α/β structures their β-sheets consist mainly of antiparallel β-strands and the catalytic serine—which is not part of a triad—is at the beginning of an α-helix adjacent to the central β-sheet [10]. Noteworthy, one member of this family, the esterase B from *Burkholderia gladioli*, has been demonstrated to be capable of hydrolyzing esters of tertiary alcohols (TAE) [11].

Other important groups of molecules with relevance to the production of fine and specialty chemicals which might be substrates for enzymes according to the present invention are those containing a thioester, amide, halide or peptide bond. Other applications of high industrial relevance are the degradation or modification or synthesis of polymers by the type of enzymes according to the present invention.

In spite of their distribution throughout humans, animals, plants and microorganisms [5], the physiological function of esterases remains to be elucidated [12]. Nevertheless, due to their high stability, the fact that they do not require cofactors, their activity in organic solvents, and their high regio- and enantioselectivity, carboxylesterases appear to be attractive biocatalysts for the production of optically pure compounds in fine chemicals synthesis [5].

Products intended for use in biological systems must often by synthesized in a particular enantiomeric form due to preferences that relate to the "handedness" (i.e., optical rotation) of the molecule. For example, only the S-form of the widely prescribed anti-inflammatory Naproxen (2-(6-methoxy-2-naphthyl)-propionic acid) shows the desired pharmacological effect. The R-form is toxic [13]. Therefore, the drug must be supplied such that the S-enantiomer, and not the R-enantiomer, is highly enriched in the final product. A similar situation exists for many other pharmaceutically relevant and agricultural chemicals. However, the synthetic chemist is often faced with a difficult problem because most chemical catalysts do not discriminate by the optical form of their substrates. In fact, it is very difficult to synthesize only a single enantiomer. Moreover, because enantiomers, by definition, have identical physical properties and differ only in the direction that they rotate the plane of polarized light, separation of individual enantiomers from a mixture of S- and R-enantiomers (deracemisation) is difficult.

Thus, the technical problem underlying the present invention was to provide means and methods for the improvement of the spectrum of enzymes capable of the conversion of a multiplicity of substrates with high reaction rates or capable of the enantioselective conversion of racemic starting material. The provision of such enzymes may increase the efficiency of the conversion and further reduce the cost for the industrial application of the produced synthons.

The solution to this technical problem is achieved by providing the embodiments characterised in the claims.

Accordingly, the present invention relates to a polynucleotide encoding an enzyme having carboxyl esterase [E.C. 3.1.1.1] activity, wherein the coding sequence is selected from the group consisting of (a) a polynucleotide encoding an amino acid sequence as depicted in any one of SEQ ID NOs: 2, 4, 6 and 8; (b) a polynucleotide having or comprising a nucleotide sequence encoding an enzyme, wherein the nucleic acid sequence is as shown in any one of SEQ ID NOs: 1, 3, 5 and 7; (c) a polynucleotide having or comprising a nucleotide sequence encoding a fragment or derivative of an enzyme encoded by a polynucleotide of (a) or (b), wherein in said derivative one or more amino acid residues are conservatively substituted compared to the amino acid sequence of (a); (d) a polynucleotide encoding an enzyme having carboxyl esterase activity which polynucleotide is at least 65% identical to a polynucleotide encoding an enzyme as shown in one of SEQ ID NOs: 2, 4, 6 and 8; (e) a polynucleotide having or comprising a nucleotide sequence the complementary strand of which hybridizes to a polynucleotide as defined in any one of (a) to (d); and (f) a polynucleotide having or comprising a nucleotide sequence being degenerate to the nucleotide sequence of the polynucleotide of (d) or (e); or the complementary strand of such a polynucleotide of (a) to (f) or fragments thereof useful as specific probes or primers.

The polynucleotides provided by the present invention are listed herein as SEQ ID NO: 1, SEQ ID NO: 3, SEQ ID NO: 5, SEQ ID NO: 7 and the polypeptides provided by the present invention are listed herein as SEQ ID NO: 2, SEQ ID NO: 4, SEQ ID NO: 6, SEQ ID NO: 8. Polynucleotide sequences and polypeptide sequences are depicted in FIGS. 1-8.

In accordance with the present invention the term "polynucleotide" defines a nucleic acid molecule consisting of more than 30 nucleotides. The group of molecules designated as "polynucleotides" also comprises complete genes. Also included by said definition are vectors such as cloning and expression vectors.

As used herein, the term "oligonucleotides" describes nucleic acid molecules consisting of at least ten and up to 30 nucleotides.

Nucleic acid molecules, in accordance with the present invention, include DNA, such as cDNA or genomic DNA, RNA (e.g. mRNA), also in synthetic or semisynthetic form, further synthetic or semisynthetic derivatives of DNA or RNA (e.g. PNA or phosphorothioates) and mixed polymers, both sense and antisense strands. They may contain additional non-natural or derivatized nucleotide bases, as will be readily appreciated by those skilled in the art. In a preferred embodiment the polynucleotide or the nucleic acid molecule(s) is/are DNA.

For the purposes of the present invention, a peptide nucleic acid (PNA) is a polyamide type of DNA analog and the monomeric units for the derivatives of adenine, guanine, thymine and cytosine are available commercially (Perceptive Biosystems). Certain components of DNA, such as phosphorus, phosphorus oxides, or deoxyribose derivatives, are not present in PNAs. As disclosed by Nielsen et al., Science 254:1497 (1991); and Egholm et al., Nature 365:666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the strong binding. In addition, it is more likely that single base mismatches can be determined with PNA/DNA hybridization because a single mismatch in a PNA/DNA 15-mer lowers the melting point (T.sub.m) by 80-20° C., vs. 40-16° C. for the DNA/DNA 15-mer duplex. Also, the absence of charge groups in PNA means that hybridization can be done at low ionic strengths and reduce possible interference by salt during the analysis.

In those embodiments where the polynucleotide comprises (rather than have) the recited sequence, additional nucleotides extend over the specific sequence either on the 5' end or the 3' end or both. Those additional polynucleotides may be of heterologous or homologous nature and may comprise stretches of about 50 to 500 nucleotides although higher or lower values are not excluded. In the case of homologous sequences, those embodiments do not include complete genomes and are generally confined to about 1500 additional nucleotides at the 5' and/or the 3' end. Additional heterologous sequences may include heterologous promoters which are operatively linked to the coding sequences of the invention.

The term "polypeptide" as used herein describes a group of molecules which consist of more than 30 amino acids. In accordance with the invention, the group of polypeptides comprises "proteins" as long as the proteins consist of a single polypeptide. Also in line with the definition the term "polypeptide" describes fragments of proteins as long as these fragments consist of more than 30 amino acids. Polypeptides may further form multimers such as dimers, trimers and higher oligomers, i.e. consisting of more than one polypeptide molecule. Polypeptide molecules forming such dimers, trimers etc. may be identical or non-identical. The corresponding higher order structures of such multimers are, consequently, termed homo- or heterodimers, homo- or heterotrimers etc. An example of a homomultimer is the enzyme according SEQ ID NO: 2. Homodimers, trimers etc. of fusion proteins, giving rise or corresponding to enzymes such as the carboxylesterases of the present invention also fall under the definition of the term "protein". Furthermore, peptidomimetics of such proteins/polypeptides wherein amino acid(s) and/or peptide bond(s) have been replaced by functional analogs are also encompassed by the invention. Such functional analogues include all known amino acids other than the 20 gene-encoded amino acids, such as selenocysteine. The terms "polypeptide" and "protein" also refer to naturally modified polypeptides/proteins wherein the modification is effected e.g. by glycosylation, acetylation, phosphorylation and the like. Such modifications are well known in the art.

The term "enzyme" defines in the context of the invention a polypeptide, polypeptides and/or protein(s), comprising either the triad of active site residues with the active site serine embedded in the consensus sequence "Sm-x-Ser-x-Gly" typical of families I, III, IV V, VI and VII of bacterial lypolytic enzymes [6] with "Sm" being a small amino acid and "x" being any amino acid or the N-terminally located active site motif "Ser-x-x-Lys" of family VIII of bacterial lypolytic enzymes [6]. Preferably, the said polypeptide, protein or fragment thereof has catalytic activity. An enzyme in accordance with the present invention is preferably defined by its capability of hydrolysing Tributyrin.

The terms "carboxylesterase" or "carboxyl-esterase" refers to an enzyme with the systematic name "carboxylic-ester hydrolase", i.e. an enzyme having an activity which may e.g. be described as hydrolysis of carboxylic esters.

Reaction: A carboxylic ester+$H_2O$=an alcohol+a carboxylate.

The IUBMB Enzyme Nomenclature refers to carboxylesterases as "EC 3.1.1.1". Examples of such carboxylesterases are: ali-esterase; B-esterase; monobutyrase; cocaine esterase; procaine esterase; methylbutyrase; vitamin A esterase; butyryl esterase; carboxyesterase; carboxylate esterase; carboxylic esterase; methylbutyrate esterase; triacetin esterase; carboxyl ester hydrolase; butyrate esterase; methylbutyrase; a-carboxylesterase; propionyl esterase; non-specific carboxylesterase; esterase D; esterase B; esterase A; serine esterase; carboxylic acid esterase; cocaine esterase.

Methods and algorithms for exchanging one or more nucleotides in the polynucleotide in item (c), supra, wherein the exchange gives rise to a conservative substitution of one or more amino acid residues in a given polypeptide are known in the art; see e.g. Barettino et al. 1994 [29], Urban et al. 1997 [30] or Seyfang & Jin 2004 [31].

In accordance with the present invention, the term "percent identity" describes the number of matches ("hits") of identical nucleotides/amino acids of two or more aligned nucleic acid or amino acid sequences as compared to the number of nucleotides making up the overall length of the nucleic acid or amino acid sequences (or the overall compared part thereof). In other terms, using an alignment, for two or more sequences or subsequences the percentage of amino acid residues or nucleotides that are the same (e.g., 60% or 65% identity) may be determined, when the (sub)sequences are compared and aligned for maximum correspondence over a window of comparison, or over a designated region as measured using a sequence comparison algorithm as known in the art, or when manually alignment and visually inspected. This definition also applies to the complement of a test sequence. Preferred polynucleotides/polypeptides in accordance with the invention are those where the described identity exists over a region that is at least about 15 to 25 amino acids or nucleotides in length, more preferably, over a region that is about 50 to 100 amino acids or nucleotides in length. Those having skill in the art will know how to determine percent identity between/among sequences using, for example, algorithms such as those based on CLUSTALW computer program (Thompson Nucl. Acids Res. 2 (1994), 4673-4680) or FASTA [21], as known in the art.

The present invention refers to polynucleotides encoding an enzyme having carboxylesterase activity. Particularly preferred are polynucleotides which are at least 65% identical to a polynucleotide encoding an enzyme as shown in one of SEQ ID NOs: 2, 4, 6, and 10. More preferred are, with increasing preference, polynucleotides which are at least 65%, at least 70%, at least 80%, at least 85%, at least 90%, at least 95%, at least 97, at least 99% sequence identity. Although the FASTDB algorithm typically does not consider internal non-matching deletions or additions in sequences, i.e., gaps, in its calculation, this can be corrected manually to avoid an over-estimation of the % identity. CLUSTALW, however, does take sequence gaps into account in its identity calculations. Also available to those having skill in this art are the BLAST and BLAST 2.0 algorithms (Altschul Nucl. Acids Res. 25 (1977), 3389-3402). The BLASTN program for nucleic acid sequences uses as defaults a word length (W) of 11, an expectation (E) of 10, M=5, N=4, and a comparison of both strands. For amino acid sequences, the BLASTP program uses as defaults a wordlength (W) of 3, and an expectation (E) of 10. The BLOSUM62 scoring matrix (Henikoff Proc. Natl. Acad. Sci., USA, 89, (1989), 10915) uses alignments (B) of 50, expectation (E) of 10, M=5, N=4, and a comparison of both strands. All those programs may be used for the purposes of the present invention. All of the above programs can be used in accordance with the invention.

The term "hybridizes/hybridizing" as used herein refers to a pairing of a polynucleotide to a (partially) complementary strand of this polynucleotide which thereby form a hybrid. Said complementary strand polynucleotides are, e.g. the polynucleotides described in item (e), supra, or parts of polynucleotides comprising at least 10, preferably at least 15 such as at least 25 consecutive nucleotides thereof, if used as primers or probes. Said complementary polynucleotides may be useful as probes in Northern or Southern blot analysis of RNA or DNA preparations, PCRs and the like or primer extension protocols respectively. In this connection, the term "fragments thereof useful as specific probes or primers" refers to nucleic acid molecules the sequence of which is uniquely fitting to (hybridizing to/complementary to preferably 100%) the sequences of the nucleic acid molecules described in accordance with the present invention, but not to prior art sequences. The skilled person can identify such fragments by simple sequence alignments. For example, if there is a 100% stretch of identity with a prior art sequence, the addition of a further nucleotide to that sequence of identity will yield a novel sequence which is encompassed by the present invention, since it is to 100% complementary to the polynucleotide of the invention but not to the prior art sequence. Hybridizing polynucleotides of the present invention to be used as a probe in Southern or Northern blot preferably comprises at least 100, more preferably at least 200, and most preferably at least 500 nucleotides in length. As regards those polynucleotides that hybridize to the complementary strand of the specifically disclosed polynucleotide sequences and retain or essentially retain carboxylesterase activity must encode at least the amino acids of the catalytic triade and the oxyanion hole of the enzyme.

Preferably, the term "polynucleotide fragment" or "fragment" refers to a fragment of the polynucleotide of the present invention lacking at least 1 nucleotide. The term "at least 1 nucleotide" means e.g. up to 1, up to 10, up to 20, up to 50 or up to 100 nucleotides. Said fragment may correspond to a 5' and/or 3' deletion of the full-length polynucleotide of the present invention. In addition or alternatively, the deletion may be located in an internal position. The deletion may affect a contiguous number of residues, however, it is also envisaged that the fragment is the polynucleotide of the present invention having deletions of various, also non-contiguous residues. Preferably, said fragment encodes a protein or polypeptide with carboxylesterase activity. The activity may not necessarily be of the same degree as the full-length or wild-type carboxylesterase as long as some activity is retained.

It is well known in the art how to perform hybridization experiments with nucleic acid molecules. Correspondingly, the person skilled in the art knows what hybridization conditions s/he has to use to allow for a successful hybridization in accordance with item (e), above. The establishment of suitable hybridization conditions is referred to in standard text books such as Sambrook, Russell "Molecular Cloning, A Laboratory Manual", Cold Spring Harbor Laboratory, N.Y. (2001); Ausubel, "Current Protocols in Molecular Biology", Green Publishing Associates and Wiley Interscience, N.Y. (1989), or Higgins and Hames (Eds.) "Nucleic acid hybridization, a practical approach" IRL Press Oxford, Washington D.C., (1985). In one preferred embodiment, the hybridization is effected is under stringent conditions.

"Stringent hybridization conditions" refers to conditions which comprise, e.g. an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulphate, and 20 μg/ml denatured, sheared salmon sperm DNA, followed by washing the filters in 0.1×SSC at about 65° C. Said conditions for hybridization are also known by a person skilled in the art as "highly stringent conditions for hybridization". Also contemplated are nucleic acid molecules that hybridize to the polynucleotides of the invention at lower stringency hybridization conditions ("low stringency conditions for hybridization"). Changes in the stringency of hybridization and signal detection are primarily accomplished through the manipulation of formamide concentration (lower percentages of formamide result in lowered stringency), salt conditions, or temperature. For example, lower stringency conditions include an overnight incubation at 37° C. in a solution comprising 6×SSPE (20×SSPE=3M NaCl; 0.2M NaH$_2$po4; 0.02M EDTA, pH 7.4), 0.5% SDS, 30% formamide, 100 μg/ml salmon sperm blocking DNA; followed by washes at 50° C. with 1×SSPE, 0.1% SDS. In addition, to achieve an even lower stringency, washes performed following stringent hybridization can be done at higher salt concentrations (e.g. 5×SSC). It is of note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility. Such modifications can generally be effected by the skilled person without further ado. A hybridization complex may be formed in solution (e.g., Cot or Rot analysis) or between one nucleic acid sequence present in solution and another nucleic acid sequence immobilized on a solid support (e.g., membranes, filters, chips, pins or glass slides to which, e.g., cells have been fixed). The embodiment recited herein above preferably refers to highly stringent conditions and alternatively to conditions of lower stringency.

The term "coding sequence" as used herein refers to the coding sequence of the carboxylesterase of the present invention or a fragment or derivative thereof. Said term relates to the genomic coding sequence as well as the coding sequence in a RNA or cDNA molecule.

When testing the carboxylesterases disclosed in the present specification, the inventors surprisingly discovered that their enzymatic activities met the requirements outlined above.

For the recombinant enzyme according to SEQ ID NO: 4 an enantioselectivity in the kinetic resolution of (rac)-menthyl acetate for the (+)-enantiomer was found with an enantiomeric excess (ee) of 100%. (−)-menthol is a key substance in the fragrancy industry and is currently produced at a scale of several thousand tons per year by fractionated crystallization from racemic menthyl benzoate [5]. Esterases from *Bacillus subtilis* and *B. stearothermophilus* hydrolyzed menthyl acetate enantioselectively (E>40 and E>100, respectively,) with a preference for (−)-menthol) but showed only low activity rates <0.2 U/mg [16].

The optical purity of chiral compounds is usually expressed as percent enantiomeric excess (% ee). % ee values can be calculated from the molar ratio of each enantiomer, Eq. 1. In practice, the peak areas of chromatographic elution for each enantiomer are obtained by gas chromatography or HPLC analysis using a chiral column and are then used to calculate % ee instead of the molar ratios.

Per definition, a racemate has a % ee value of 0, optically pure compounds have a % ee value of 100.

$$\% \ ee = \frac{X_A - X_B}{X_A + X_B} * 100 \quad \text{Eq.. 1}$$

$X_{A\_}$=Concentration of enantiomer A; $X_{B\_}$=Concentration of enantiomer B Enzymatic syntheses of optically active compounds either start from racemic mixtures or from prostereogenic (prochiral) precursors. The latter ideally yields a product with 100% ee at 100% yield. In contrast, a kinetic resolution will only lead to a yield of 50%. Methods to increase the yield include racemization of the non-wanted enantiomer, by using a racemase or chemical racemization or by performing a so-called dynamic kinetic resolution (DKR). The requirements for a DKR are: (1), the substrate must racemize faster than the subsequent enzymatic reaction, (2), the product must not racemize, and (3), as in any asymmetric synthesis, the enzymatic reaction must be highly stereoselective.

The stereo-preference (enantio-preference) of an enzyme is routinely described by the enantiomeric excess (ee) of the product enantiomers after a reaction has taken place. However, there are alternative ways to describe the enantioselectivity of an enzyme. In a kinetic resolution, the enantiomeric purity of the product and starting material varies as the reaction proceeds. To more conveniently compare kinetic resolutions, Charles Sih's group developed equations to calculate their inherent enantioselectivity [14, 15]. This enantioselectivity, called the enantiomeric ratio, E, measures the ability of the enzyme to distinguish between enantiomers. A non-selective reaction has an E of 1, while resolutions with E's above 20 (better E>50) are useful for synthesis. To calculate E, one measures two of the three variables: enantiomeric purity of the starting material ($ee_s$), enantiomeric purity of the product ($ee_p$), and extent of conversion (c) and uses one of the three equations below (Eq. 2). Often enantiomeric purities are more accurately measured than conversion; in these cases, the third equation is more accurate. Note that these equations are only applicable to irreversible reactions. In other cases, the equilibrium constant must be determined and alternative equations must be used.

$$E = \frac{\ln[1 - c(1 + ee_p)]}{\ln[1 - c(1 - ee_p)]};$$

$$E = \frac{\ln[(1 - c)(1 - ee_s)]}{\ln[(1 - c)(1 + ee_s)]};$$

$$E = \frac{\ln\left[\frac{1 - ee_s}{1 + (ee_s/ee_p)}\right]}{\ln\left[\frac{1 + ee_s}{1 + (ee_s/ee_p)}\right]}$$

Eq. 2

High E values (≥100) are less accurately measured than low or moderate E values because the enantiomeric ratio is a logarithmic function of the enantiomeric purity. When E≥100, small changes in the measured enantiomeric purities give large changes in the enantiomeric ratio. Thus, it is recommended to report high enantioselectivity only as E≥100. However, for many possible applications the adequate enzyme is not yet available due to limitations of the known enzymes with respect to substrate specificity and enantioselectivity.

The recombinant enzyme according to SEQ ID NO: 2 and 6 hydrolyzed rac-cis-3,5-diacetoxy-1-cyclopenten with an ee-value of 100% at a conversion of 24% and 100%, respectively, for the preferred enantiomer. The enantiopreference was not determined due to the lack of enantiopure reference compounds. The recombinant enzymes according to SEQ ID NO. 4 and 8 hydrolyzed this substrate with an ee-value of 66% and 76% at 12% and 100% conversion, respectively. Chiral cyclopentanoid building blocks are used for the synthesis of carbacyclic prostaglandin 12 derivatives—potential therapeutic agents for the treatment of thrombotic diseases [17].

The enzyme according to SEQ ID NO: 4 hydrolyzed the acetic acid ester of rac-trans-1,2-cyclohexanediol enantioselectively with an ee of 38% at 100% conversion of the preferred enantiomer. The enantiopreference was not determined due to the lack of enantiopure reference compounds.

The enzymes according to SEQ ID NO: 2 and 4 were capable of hydrolyzing acetic acid esters of rac-1-octin-3-ol, of R-(+)-3-chlor-1-phenyl-1-propanol, and of trimethylsilylbutinol.

The enzyme according to SEQ ID NO: 4 was capable of converting acetic acid esters of cis-1,2-cyclohexanediol and isopropylidene glycerol. Isopropylidene glycerol is widely used as a pharmaceutical synthon, especially for the production of β-blockers.

The enzymes according to SEQ ID NOs: 2 and 4 hydrolyzed the p-nitrophenyl (pNP) esters of different substrates with importance for the production of pharmaceutical synthons. Cyclohexanoate was converted with specific activities of 50.0 U/mg and 16.8 U/mg, respectively. The pNP-ester of benzoate was hydrolyzed with specific activities of 9.4 U/mg and 12.1 U/mg, respectively. The pNP-esters of 3-phenylbutanoate and 2-(3-benzoylphenyl)propanoate were hydrolyzed by the recombinant enzyme according to SEQ ID NO: 2 with specific activities of 31.6 U/mg and 26.7 U/mg, respectively. The recombinant enzyme according to SEQ ID NO: 4 showed specific activities for these substrates of 1.0 and 0.8 U/mg, respectively. The recombinant enzyme according to SEQ ID NO: 2 converted the pNP-ester of 2-phenylpropanoate with a specific activity of 21.0 U/mg. Furthermore, this enzyme hydrolyzed the nonsteroidal anti-inflammatory drugs ibuprofen, 2-(4-isobutylphenyl)propanoate and naproxen, 2-(6-methoxynaphtalen-2-yl) propanoate with specific activities of 7.2 U/mg and 26.7 U/mg, respectively.

The recombinant enzyme according to SEQ ID NO: 2 showed an exceptionally high specific activity towards pNP-valerate of 425.7 U/mg. The esterases from *Xanthomonas vesicatoria* [18], *Pseudomonas* sp. B11-1 [19] and *Aeromonas hydrophila* MCC-2 [20] were reported to convert this substrate with a specific activity of 10.5 U/mg, 64 U/mg and 86.3 U/mg, respectively.

Surprisingly, the enzyme according to SEQ ID NO: 2 was able to convert the secondary ester 7-(3-octylcarboxy-(3-hydroxy-3-methyl-butyloxy))-coumarine as determined by a fingerprint analysis (see example 7). This substrate is very unreactive and almost never converted to any measurable extent by other enzymes.

The enzymes according to SEQ ID NO: 6 was denoted to belong to family IV of bacterial lipolytic enzymes. The enzymes according to SEQ ID NO: 8 was denoted to belong to the family V of bacterial lipolytic enzymes, those according to SEQ ID NO: 2 and 4 were denoted to be members of family VIII. The similarity of the polynucleotides according to SEQ ID NOs: 1, 3, 5, and 7 to other polynucleotides is shown in tables 1-4. The analysis was performed using the Fasta algorithm [21] using: GenBank database [23], Release 152.0, (released on 18 Feb. 2005).

TABLE 1

Sequence identity of the enzyme according to SEQ ID No. 1 (EstA3)

| next neighbour | gene identifier | organism | identity | overlap | reference |
|---|---|---|---|---|---|
| epothilone biosynthesis gene cluster, ORF2 | AF210843 | *Sorangium cellulosum* strain So ce90 | 53.4% | 990 nt (1120-160:1974-2934) | [27] |

TABLE 1-continued

Sequence identity of the enzyme according to SEQ ID No. 1 (EstA3)

| next neighbour | gene identifier | organism | identity | overlap | reference |
|---|---|---|---|---|---|
| EstBL esterase with B-lactamase fold | AY965997 | *Burkholderia cepacia* UWC10 | 55.6% | 360 nt (331-679:491-839) | Rashamuse & Cowan, unpublished |

TABLE 2

Sequence identity of the enzyme according to SEQ ID No. 3 (EstCE1)

| next neighbour | gene identifier | organism | identity | overlap | reference |
|---|---|---|---|---|---|
| Protocechuate 3,4-dioxygenase beta- | U33634 | *Burkholderia gladioli* | 60.0% | 1121 nt (1146-38:1574-2679*) | [28] |
| lipase lip-1 | X61673 | *Pseudomonas* sp. nov 109 | 57.0% | 1130 nt (43-1145:61-1162) | Ihara et al., unpublished |

TABLE 3

Sequence identity of the enzyme according to SEQ ID No. 5 (EstCL1)

| next neighbour | gene identifier | organism | identity | overlap | reference |
|---|---|---|---|---|---|
| esterase HDE | AB029896 | *Oleomonas sagaranensis* | 57.3% | 710 nt (175-852:166-864) | Mizuguchi et al, unpublished |
| lipase LipP | AF034088 | *Pseudomonas* sp. B11-1 | 57.7% | 638 nt (241-859:223-850) | [19] |

TABLE 4

Sequence identity of the enzyme according to SEQ ID No. 7 (EstCL2)

| next neighbour | gene identifier | organism | identity | overlap | reference |
|---|---|---|---|---|---|
| PBS(A) depolymerase | AB066349 | *Acidovorax delafieldii* | 58.2% | 361 nt (203-561:233-591) | [29] |
| lipase | AL939106.1 | *Streptomyces coelicolor* A3(2) | 62.3% | 220 nt (415-202:166822-167038) | [30] |

In a preferred embodiment of the present invention said coding region is fused with a heterologous or homologous polynucleotide.

This heterologous or homologous polynucleotide may or may not be or comprise a coding region. The polynucleotide and/or the encoded enzyme having carboxylesterase activity is/are either heterologous with respect to the host or is/are homologous with respect to the host but located in a different genomic environment than the naturally occurring counterpart of said nucleotide sequence. A polynucleotide is "heterologous" when it is derived from a cell or organism belonging to a different strain (preferably to a different species) with regard to the origin of the sequence encoding the carboxylesterase of the present invention. In contrast, a polynucleotide is "homologous" when it is derived from the same cell or organism as the sequence encoding the carboxylesterase of the invention. "Homologous" with respect to the host but located in a different genomic environment than the naturally occurring counterpart of said nucleotide sequence means that, if the nucleotide sequence is homologous with respect to the host (i.e. is naturally present in the same strain or species), it is not located in its natural location in the genome of said host. In particular it may be surrounded by different genes. In this case the nucleotide sequence may be either under the control of its own promoter or under the control of a heterologous promoter. The location of the introduced nucleic acid molecule can be determined by the skilled person by using methods well-known in the art, including Southern blotting. The polynucleotide(s) according to the invention which is/are present in the host may either be integrated into the genome of the host or be maintained extrachromosomally. With respect to the first option, it is also to be understood that the polynucleotide of the invention can be used to restore or create a mutant gene via homologous recombination.

It is known to the skilled person that certain bivalent cations have a modulating effect on the activity of the carboxyl esterase of the present invention. In this regard, it is for example noteworthy that the catalytic activity of the enzyme of SEQ ID NO: 2 of the present invention is stimulated in the presence of $Co^{2+}$ by about 130%. It has been observed that other bivalent cations like $Ca^{2+}$, $Cu^{2+}$ $Mg^{2+}$, $Zn^{2+}$ $Rb^{2+}$ and EDTA have a inhibitory effect on enzymes such as the carboxyl esterase of SEQ ID NO: 2. Surprisingly, as far as the enzyme of SEQ ID NO: 4 (EstCE1) is concerned, the present inventors observed a reversed modulatory effect in the presence of bivalent cations such as $Ca^{2+}$ and $Mg^{2+}$, which resulted in a stimulation of the catalytic activity. With regard to EstCE1, the present inventors have observed a stimulatory effect amounting to 118% and 108%, respectively.

In a more preferred embodiment of the present invention, said heterologous or homologous polynucleotide encodes a polypeptide. Examples of heterologous polypeptides are NusA from *E. coli*, glutathion S-transferase from *Schistosoma japonicum* or the maltose binding protein from *E. coli* all of which might increase the solubility of the carboxylesterase. The present invention also relates to a vector containing the polynucleotide of the present invention. Preferably, the vector is a plasmid, cosmid, virus, bacteriophage or another vector used e.g. conventionally in genetic engineering.

The polynucleotide of the present invention may be inserted into several commercially available vectors. Non-limiting examples include prokaryotic plasmid vectors, such as the pUC-series, pBluescript (Stratagene), the pET-series of expression vectors (Novagen) or pCRTOPO (Invitrogen) and vectors compatible with an expression in mammalian cells like pREP (Invitrogen), pcDNA3 (Invitrogen), pCEP4 (Invitrogen), pMC1 neo (Stratagene), pXT1 (Stratagene), pSG5 (Stratagene), EBO-pSV2neo, pBPV-1, pdBPVMMTneo, pRSVgpt, pRSVneo, pSV2-dhfr, pIZD35, pLXIN, pSIR (Clontech), pIRES-EGFP (Clontech), pEAK-10 (Edge Biosystems) pTriEx-Hygro (Novagen) and pCINeo (Promega). Examples for plasmid vectors suitable for *Pichia pastoris* comprise e.g. the plasmids pAO815, pPIC9K and pPIC3.5K (all Intvitrogen).

The polynucleotide of the present invention referred to above may also be inserted into vectors such that a translational fusion with another polynucleotide is generated. The other polynucleotide may encode a protein which may e.g. increase the solubility and/or facilitate the purification of the fusion protein. Non-limiting examples include pET32, pET41, and pET43.

For vector modification techniques, see Sambrook and Russel (2001), loc. cit. Generally, vectors can contain one or more origin of replication (ORI) and inheritance systems for cloning or expression, one or more markers for selection in the host, e.g., antibiotic resistance, and one or more expression cassettes. Suitable origins of replication (ori) include, for example, the Col E1, the SV40 viral and the M 13 origins of replication.

The coding sequences inserted in the vector can e.g. be synthesized by standard methods, or isolated from natural sources. Ligation of the coding sequences to transcriptional regulatory elements and/or to other amino acid encoding sequences can be carried out using established methods. Transcriptional regulatory elements (parts of an expression cassette) ensuring expression in prokaryotes or eukaryotic cells are well known to those skilled in the art. These elements comprise regulatory sequences ensuring the initiation of the transcription (e.g., translation initiation codon, promoters, enhancers, and/or insulators), internal ribosomal entry sites (IRES) (Owens, Proc. Natl. Acad. Sci. USA 98 (2001), 1471-1476) and optionally poly-A signals ensuring termination of transcription and stabilization of the transcript. Additional regulatory elements may include transcriptional as well as translational enhancers, and/or naturally-associated or heterologous promoter regions. Preferably, the polynucleotide of the invention is operatively linked to such expression control sequences allowing expression in prokaryotes or eukaryotic cells. The vector may further comprise nucleotide sequences encoding secretion signals as further regulatory elements. Such sequences are well known to the person skilled in the art. Furthermore, depending on the expression system used, leader sequences capable of directing the expressed polypeptide to a cellular compartment may be added to the coding sequence of the polynucleotide of the invention. Such leader sequences are well known in the art.

Possible examples for regulatory elements ensuring the initiation of transcription comprise the cytomegalovirus (CMV) promoter, SV40-promoter, RSV-promoter (Rous Sarcoma Virus), the lacZ promoter, the gai10 promoter, human elongation factor 1α-promoter, CMV enhancer, CaM-kinase promoter, the *Autographa californica* multiple nuclear polyhedrosis virus (AcMNPV) polyhedral promoter or the SV40-enhancer. For the expression in prokaryotes, a multitude of promoters including, for example, the tac-lac-promoter, the lacUV5 or the trp promoter, has been described. Examples for further regulatory elements in prokaryotes and eukaryotic cells comprise transcription termination signals, such as SV40-poly-A site or the tk-poly-A site or the SV40, lacZ and AcMNPV polyhedral polyadenylation signals, downstream of the polynucleotide.

Furthermore, it is preferred that the vector of the invention comprises a selectable marker. Examples of selectable markers include neomycin, ampicillin, and hygromycin resistance and the like. Specifically-designed vectors allow the shuttling of DNA between different hosts, such as bacteria-fungal cells or bacteria-animal cells.

An expression vector according to this invention is capable of directing the replication, and the expression, of the polynucleotide and encoded enzyme of this invention. Suitable expression vectors which comprise the described regulatory elements are known in the art such as Okayama-Berg cDNA expression vector pcDV1 (Pharmacia), pRc/CMV, pcDNA1, pcDNA3 (In-Vitrogene, as used, inter alia in the appended examples), pSPORT1 (GIBCO BRL) or pGEMHE (Promega), or prokaryotic expression vectors, such as lambda gt11, pJOE, the pBBR1-MCS-series, pJB861, pBSMuL, pBC2, pUCPKS, pTACT1 or, preferably, the pET vector (Novagen).

The nucleic acid molecules of the invention as described herein above may be designed for direct introduction or for introduction via liposomes, phage vectors or viral vectors (e.g. adenoviral, retroviral) into the cell. Additionally, baculoviral systems or systems based on Vaccinia Virus or Semliki Forest Virus can be used as eukaryotic expression system for the nucleic acid molecules of the invention.

The present invention also relates to a host, genetically engineered with the polynucleotide of the present invention or the vector of the present invention. Said host may be produced by introducing said polynucleotide or vector(s) into a host which upon its/their presence mediates the expression of the enzyme having carboxylesterase activity. The host may be any prokaryote or eukaryotic cell. A suitable eukaryotic host may be a mammalian cell, an amphibian cell, a fish cell, an insect cell a fungal cell or a plant cell. A eukaryotic cell may be an insect cell such as a *Spodoptera frugiperda* cell, a yeast cell such as a *Saccharomyces cerevisiae* or *Pichia pastoris* cell, a fungal cell such as an *Aspergillus* cell or a vertebrate cell. In the latter regard, it is preferred that the cell is a mammalian cell such as a human cell. The cell may be a part of a cell line.

Suitable prokaryotes/bacteria are those generally used for cloning/expression like *E. coli* (e.g., *E. coli* strains HB101, DH5a, XL1 Blue, Y1090 and JM101), *Salmonella typhimurium, Serratia marcescens, Burkholderia glumae, Pseudomonas putida, Pseudomonas fluorescens, Pseudomonas stutzeri, Streptomyces lividans, Lactococcus lactis, Mycobacterium smegmatis* or *Bacillus subtilis*. A suitable eukaryotic host may be a mammalian cell, an amphibian cell, a fish cell, an insect cell, a fungal cell or a plant cell. Preferred examples for hosts to be genetically engineered with the polynucleotide of the invention are *E. coli* and *Bacillus subtilis*.

In a preferred embodiment of the present invention, the host is a prokaryotic host selected from the group consisting of *E. coli*, *Bacillus* sp., *Pseudomonas* sp., *Streptomyces* sp., *Mycobacterium* sp., *Caulobacter* sp., *Rhodobacter* sp., *Lactococcus* sp., *Burkholderia sp*, *Rhizobium* sp., *Sinorhizobium* sp. and *Ralstonia* sp.

In another preferred embodiment of the present invention, the host of the present invention expresses the polypeptide encoded by the polynucleotide of the present invention or the vector of the present invention and one or more additional enzyme(s) wherein said enzymes in toto catalyze a multi-step conversion of a substrate or contribute thereto.

The present invention also relates to a process for producing a polypeptide having carboxyl esterase [E.C. 3.1.1.1] activity, comprising culturing the host of the present invention and recovering the polypeptide produced by said host.

A large number of suitable methods exist in the art to produce polypeptides (or fusion proteins) in appropriate hosts. If the host is a unicellular organism such as a prokaryote, a mammalian or insect cell, the person skilled in the art can revert to a variety of culture conditions. Conveniently, the produced protein is harvested from the culture medium, lysates of the cultured organisms or from isolated (biological) membranes by established techniques. In the case of a multicellular organism, the host may be a cell which is part of or derived from a part of the organism, for example said host cell may be the harvestable part of a plant. A preferred method involves the recombinant production of protein in hosts as indicated above. For example, nucleic acid sequences comprising the polynucleotide according to the invention can be synthesized by PCR, inserted into an expression vector. Subsequently a suitable host may be transformed with the expression vector. Thereafter, the host is cultured to produce the desired polypeptide(s), which is/are isolated and purified.

An alternative method for producing the carboxylesterase of the invention is in vitro translation of mRNA. Suitable cell-free expression systems for use in accordance with the present invention include rabbit reticulocyte lysate, wheat germ extract, canine pancreatic microsomal membranes, *E. coli* S30 extract, and coupled transcription/translation systems such as the TNT-system (Promega). These systems allow the expression of recombinant polypeptides upon the addition of cloning vectors, DNA fragments, or RNA sequences containing coding regions and appropriate promoter elements.

In addition to recombinant production, fragments of the protein, the fusion protein or fragments of the invention may e.g. be produced by direct peptide synthesis using solid-phase techniques (cf Stewart et al. (1969) Solid Phase Peptide Synthesis; Freeman Co, San Francisco; Merrifield, J. Am. Chem. Soc. 85 (1963), 2149-2154). Synthetic protein synthesis may be performed using manual techniques or by automation. Automated synthesis may be achieved, for example, using the Applied Biosystems 431A Peptide Synthesizer (Perkin Elmer, Foster City Calif.) in accordance with the instructions provided by the manufacturer. Various fragments may be chemically synthesized separately and combined using chemical methods to produce the full length molecule. As indicated above, chemical synthesis, such as the solid phase procedure described by Houghton Proc. Natl. Acad. Sci. USA (82) (1985), 5131-5135, can be used.

Protein isolation and purification can be achieved by any one of several known techniques; for example and without limitation, ion exchange chromatography, gel filtration chromatography and affinity chromatography, high pressure liquid chromatography (HPLC), reversed phase HPLC, and preparative disc gel electrophoresis. Protein isolation/purification techniques may require modification of the proteins of the present invention using conventional methods. For example, a histidine tag can be added to the protein to allow purification on a nickel column. Other modifications may cause higher or lower activity, permit higher levels of protein production, or simplify purification of the protein.

The present invention also relates to a process for producing bacteria or eukaryotic cells capable of expressing a polypeptide having carboxyl esterase [E.C. 3.1.1.1] activity, the process comprising genetically engineering bacteria or eukaryotic cells with the vector of the present invention. Said polypeptide may comprise additional N- or C-terminal amino acid sequences. Such polypeptides are sometimes also referred to as fusion proteins. The term "genetic engineering" refers to the process of bringing into a cell genetic information or modifying the genetic information of a cell. This is generally accomplished by transfecting or transforming a host cell with a nucleic acid molecule. Introduction of a construct into the host cell can be effected by calcium phosphate transfection, DEAE-dextran mediated transfection, cationic lipid-mediated transfection, electroporation, transduction, infection or other methods. Such methods are described in many standard laboratory manuals, such as Sambrook et al., "Molecular Cloning, A Laboratory Manual"; ISBN: 0879695765, CSH Press, Cold Spring Harbor, 2001. Said nucleic acid molecule introduced into the host cell comprises an open reading frame encoding the polypeptide of the present invention. The present invention also relates to a polypeptide comprising the amino acid sequence encoded by a polynucleotide of the present invention or obtainable by the process of the present invention. In addition of residues derived from a carboxylesterase, the polypeptide of the present invention may contain additional, heterologous sequences. Often, but not necessarily, these additional sequences will be located at the N- or C-terminal end of the polypeptide, in other words the polypeptide may be a fusion protein. It may be convenient to initially express the polypeptide as a fusion protein from which the additional amino acid residues can be removed, e.g. by expression of a proteinase capable of specifically trimming the polypeptide of the present invention. The additional heterologous sequences may help in the expression or purification of the present invention. In addition, heterologous sequences may assist in attaching the polypeptide of the present invention to a carrier.

The present invention also relates to an antibody specifically binding to the polypeptide of the present invention. It is preferred that the antibody binds to the polypeptides or fusion protein of the invention in the form having carboxylesterase activity. In the embodiment of the antibody which specifically binds to the fusion protein of the invention, the antibody specifically binds either to epitopes formed by carboxylesterase residues within of the fusion protein. The antibody may however also bind to epitopes formed by the stretch of amino acids including the fusion point of the two heterologous polypeptides. This epitopes are characteristic (unique) for the fusion protein of the invention.

The antibody of the present invention can be, for example, polyclonal or monoclonal. The term "antibody" also comprises derivatives or fragments thereof which still retain the binding specificity. Techniques for the production of antibodies are well known in the art and described, e.g. in Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999. These antibodies can be used, for example, for the immunoprecipitation, affinity purification and immunolocalization of the polypeptides or fusion proteins of the invention as well as for the monitoring of the presence and amount of such polypeptides, for example, in cultures of recombinant prokaryotes or eukaryotic cells or organisms.

The antibody of the invention also includes embodiments such as chimeric, single chain and humanized antibodies, as well as antibody fragments, like, inter alia, Fab fragments. Antibody fragments or derivatives further comprise F(ab')$_2$, Fv or scFv fragments; see, for example, Harlow and Lane (1988) and (1999), loc. cit. Various procedures are known in the art and may be used for the production of such antibodies and/or fragments. Thus, the (antibody) derivatives can be produced by peptidomimetics. Further, techniques described for the production of single chain antibodies (see, inter alia, U.S. Pat. No. 4,946,778) can be adapted to produce single chain antibodies specific for polypeptide(s) and fusion proteins of this invention. Also, transgenic animals may be used to express humanized antibodies specific for polypeptides and fusion proteins of this invention. Most preferably, the antibody of this invention is a monoclonal antibody. For the preparation of monoclonal antibodies, any technique which provides antibodies produced by continuous cell line cultures can be used. Examples for such techniques include the hybridoma technique (Köler and Milstein Nature 256 (1975), 495-497), the trioma technique, the human B-cell hybridoma technique (Kozbor, Immunology Today 4 (1983), 72) and the EBV-hybridoma technique to produce human monoclonal antibodies (Cole et al., Monoclonal Antibodies and Cancer Therapy, Alan R. Liss, Inc. (1985), 77-96). Surface plasmon resonance as employed in the BIAcore system can be used to increase the efficiency of phage antibodies which bind to an epitope of an polypeptide of the invention (Schier, Human Antibodies Hybridomas 7 (1996), 97-105; Malmborg, J. Immunol. Methods 183 (1995), 7-13). It is also envisaged in the context of this invention that the term "antibody" comprises antibody constructs which may be expressed in cells, e.g. antibody constructs which may be transfected and/or transduced via, inter alia, viruses or plasmid vectors.

The antibody described in the context of the invention is capable to specifically bind/interact with an epitope of the polypeptides or fusion protein of the invention. The term "specifically binding/interacting with" as used in accordance with the present invention means that the antibody does not or essentially does not cross-react with an epitope of similar structure. Thus, the antibody does not bind to prior art carboxylesterase of the present invention. Cross-reactivity of a panel of antibodies under investigation may be tested, for example, by assessing binding of said panel of antibodies under conventional conditions to the epitope of interest as well as to a number of more or less (structurally and/or functionally) closely related epitopes. Only those antibodies that bind to the epitope of interest in its relevant context (e.g. a specific motif in the structure of a protein) but do not or do not essentially bind to any of the other epitope are considered specific for the epitope of interest and thus to be antibodies in accordance with this invention. Corresponding methods are described e.g. in Harlow and Lane, 1988 and 1999, loc cit.

The antibody specifically binds to/interacts with conformational or continuous epitopes which are unique for the polypeptides or fusion protein of the invention. A conformational or discontinuous epitope is characterized for polypeptide antigens by the presence of two or more discrete amino acid residues which are separated in the primary sequence, but come together on the surface of the molecule when the polypeptide folds into the native protein/antigen (Sela, (1969) Science 166, 1365 and Layer, (1990) Cell 61, 553-6). The two or more discrete amino acid residues contributing to the epitope are present on separate sections of one or more polypeptide chain(s). These residues come together on the surface of the molecule when the polypeptide chain(s) fold(s) into a three-dimensional structure to constitute the epitope. In contrast, a continuous or linear epitope consists of two or more discrete amino acid residues which are present in a single linear segment of a polypeptide chain.

The present invention also relates to a primer which specifically hybridizes under stringent conditions to a polynucleotide of the present invention. Said primer is at least 10, more preferably at least 15, further preferably at least 20, furthermore preferably at least 25 nucleotides in length. Preferably said primer is up to 30, more preferably up to 35, further preferably up to 40 nucleotides in length.

The term "primer" when used in the present invention means a single-stranded nucleic acid molecule capable of annealing to the nucleic acid molecule of the present invention and thereby being capable of serving as a starting point for amplification or elongation. For an amplification reaction it is preferred that a pair of primers is elected. According to the present invention the term "pair of primers" means a pair of primers that are with respect to a complementary region of a nucleic acid molecule directed in the opposite direction towards each other to enable, for example, amplification by polymerase chain reaction (PCR).

The term "amplifying" refers to repeated copying of a specified sequence of nucleotides resulting in an increase in the amount of said specified sequence of nucleotides and allows the generation of a multitude of identical or essentially identical (i.e. at least 95% more preferred at least 98%, even more preferred at least 99% and most preferred at least 99.5% such as 99.9% identical) nucleic acid molecules or parts thereof. Such methods are well established in the art; see Sambrook et al. "Molecular Cloning, A Laboratory Manual", 2nd edition 1989, CSH Press, Cold Spring Harbor. They include polymerase chain reaction (PCR) and modifications thereof, ligase chain reaction (LCR) to name some preferred amplification methods.

It is also preferred that the nucleic acid molecule of the invention, also including the primer of the present invention, is labelled. The label may, for example, be a radioactive label, such as $^{32}$P, $^{33}$P or $^{35}$S. In a preferred embodiment of the invention, the label is a non-radioactive label, for example, digoxigenin, biotin and fluorescence dye or a dye.

The present invention also relates to a composition comprising the polynucleotide of the present invention, the vector of the present invention, the host of the present invention, the polypeptide of the present invention, the antibody of the present invention and/or one or more primers of the present invention. The term "composition", as used in accordance with the present invention, relates to a composition which comprises at least one of the recited compounds. It may, optionally, comprise further molecules capable of altering the characteristics of the compounds of the invention thereby, for example, suppressing, stabilizing, blocking, modulating and/or activating their function. The composition may be in solid, liquid or gaseous form and may be, inter alia, in the form of (a) powder(s), (a) tablet(s), (a) solution(s) or (an) aerosol(s).

The present invention also relates to a method for the production of an optical active compound comprising allowing the enantioselective conversion of a racemic starting material by a polypeptide of the present invention. ee-values of 100% were determined for the conversion of rac-menthylacetate by the enzyme according to SEQ ID NO: 4, for the conversion of rac-isopropylideneglycerol acetate by the enzyme according to SEQ ID NO:6 and for the conversion of rac-cis-3,5-diacetoxy-1-cyclopenten by the enzymes according to SEQ ID NO: 2 and 6 as outlined in example 8. The term "optically active" as used herein describes the capability of a molecule to rotate the plane of polarization of a light wave. This capability is associated with asymmetry in the molecule. It is very often the result of a chiral centre. The term "enantioselective conversion" refers to the selective conversion of a chiral or prochiral substrate into an enantioenriched or enantiopure product.

In a preferred embodiment of the present invention, said optical active compound is (+)-menthol and the racemic starting material is rac-menthyl acetate.

In another preferred embodiment of the present invention said racemic starting material (educt) is produced by catalysis of a conversion by one or more different enzymes and/or the optical active compound (product) is the starting material (educt) for a further conversion by one or more different enzyme(s).

BRIEF DESCRIPTION OF THE DRAWINGS

FIG. 1: SEQ ID NO: 1 (EstA3)
FIG. 2: SEQ ID NO: 2 (EstA3)
FIG. 3: SEQ ID NO: 3 (EstCE1)
FIG. 4: SEQ ID NO: 4 (EstCE1)
FIG. 5: SEQ ID NO: 5 (EstCL1)
FIG. 6: SEQ ID NO: 6 (EstCL1)
FIG. 7: SEQ ID NO: 7 (EstCL2)
FIG. 8: SEQ ID NO: 8 (EstCL2)
FIG. 10: Enzyme activity of enzymes according to SEQ ID NO: 2, 4 and 6 at various pH values, determined with three different buffer systems as indicated.
FIG. 11: Activity of enzymes according to SEQ ID NO: 2 and 4 at various temperatures.
FIG. 12: Thermal stability of the enzymes according to SEQ ID NO: 2 and 4 at various temperature as indicated, assayed for 1 hour.

Figure 9:
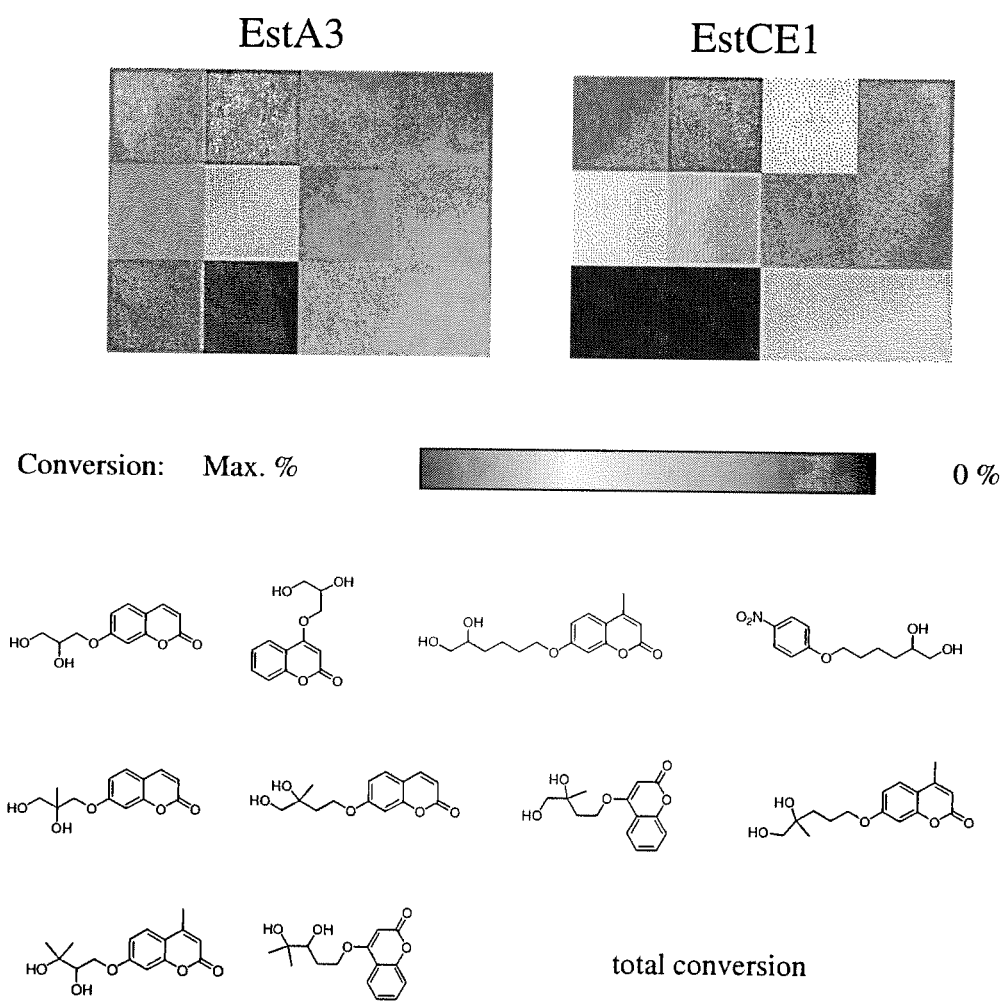
FIG. 9: Fingerprint analysis of the conversion of 10 different model substrates by the enzymes according to SEQ ID NO: 2 and 4. The substrate with highest conversion was set as maximum (red), the strength of conversion of the other substrates is indicated according to the color scheme. The colored boxes represent the substrates 1-10 according to the order shown, the stereocenter of each molecule is indicated with an asterisk. The total conversion in percent (%) is color-coded in the two squares at lower right.

The invention is illustrated by the following examples but it should be understood that this invention is not limited thereto or thereby.

EXAMPLE 1

Screening

DNA isolation methods were based on the method described previously [24]. Libraries were prepared in the cosmid vector pWE15 which has kanamycin and ampicillin resistance (Stratagene, La Jolla, Calif.) using protocols as provided by the manufacturer. DNA fragments (20-40 kb) obtained after partial Sau3AI digestion were ligated into the BamHI restriction site of the cosmid vector. Phage packaging mixes were obtained from Stratagene (La Jolla, Calif.), and infection of E. coli VCS257 was performed according to the manufacturer's protocol.

EXAMPLE 2

Heterologous Expression

The estCE1, estA3, estCL1 and estCL2 genes were amplified from cosmid DNAs using PCR in 35 cycles with primer pairs ESTCE1-for (5'-GGC ATA TGT CGA TAG CGG ATC AGT CA-3') and ESTCE1-rev (5'-GGA TCC TTA GCG AGT AGG TTC GTT TG-3'), ESTA3-for (5'-GCG GAT CCA TGA GCG CCG AAG AAC TAG GG-3') and ESTA3-rev (5'-CGA AGC TTG GCG GCG AGC GCG CTG TA-3'), estcl1up (5'-AGA GAC CAT ATG ACC GAT CCC TAT GTG CG-3') and estcl1dw (5'-CGG TTT GGA TCC TCA TGC TTC TGC CAT AAC-3'), estCL2up (5'-ACT ATC CAT ATG AAA AGA AAA ACA ATC TTC-3') and estCL2dwchis (5'-TTA GTT AAG CTT CTG CGG CAA ACT TGC AG-3'), respectively (SEQ ID NOs:9-16). Primers were designed to introduce a 3'-BamHI restriction site and a 5'-NdeI site into the cloned fragment of estCE1, estCL1 and estCL2 and a 3'-HindIII site and a 5'-BamHI site into estA3, respectively. To increase cloning efficiency the PCR fragments were first ligated into pBSK+ (Stratagene, La Jolla, Calif.), then excised with Nde/I and BamHI, and ligated into pET19b (Novagen, Madison, USA) for estCE1 or into pET16a (Novagen, Madison, USA) for estCL1 or into pET22b (Novagen, Madison, USA) for estCL2 and exised with BamHI and HindIII and ligated into pET24c (Novagen, Madison, USA) for estA3, respectively. The plasmids carrying the estCE1, estA3, estCL1 and the estCL2 sequence were designated pET19b-EstCE1, pET24c-EstA3, p16estCL1 and p22estCL22, respectively. Freshly transformed E. coli BL21(DE3) cells carrying the respective plasmid were used to overproduce the corresponding proteins. Cultures were grown at 37° C. to an optical density of 0.5 at 600 nm, and production of the recombinant protein was induced by the addition of 0.5 mM isopropyl-beta-D-thiogalactopyranoside (IPTG). After 4-5 h, cells were harvested, disrupted in a French pressure cell, and the enzymes were purified from the soluble fraction.

EXAMPLE 3

Purification

Extracts were loaded on Protino-Ni-2000 prepacked columns, and chromatography was done as specified by the manufacturer (Machery & Nagel, Düren, Germany). Protein extracts were then dialyzed overnight against 50 mM $NaH_2PO_4$/300 mM NaCl (pH 7.5). The resulting protein fractions were analyzed by 12% SDS polyacrylamide gel electrophoresis and Western-immunoblotting using 6-His-specific antibodies. EstA3 and EstCE proteins were further purified by size exclusion chromatography (Superdex 200 prep grade, column: HiLoad16/60, 50 mM $NaH_2PO_4$/300 mM NaCl 1 ml/min) to homogeneity.

EXAMPLE 4

Determination of Enyzme Activity

Enzyme activity tests were performed by incubating the enzyme with 4 mM substrate at 45° C. in 100 mM Tris-HCl buffer at pH 7.2, unless otherwise indicated. The reaction was measured at 410 nm. One unit is defined as the amount of enzyme catalyzing the appearance of 1 µmol of free p-nitrophenol/min. Enzyme activity against pNP-acylesters (butyrate, valerate, caproate, octanoate, decanoate and palmitate) was tested under the above conditions. The recombinant enzymes according to SEQ ID NO.2 and 4 showed highest activity towards short chain fatty acids ($C_4$) while activity towards long chain fatty acids (>$C_8$) was much lower. The enzyme according to SEQ ID NO: 6 converted pNP-caproate with a specific activity of 80.0 U/mg. The results are shown in Table 5.

TABLE 5

Activity of the enzymes with various pNP-acylesters of different chain length

| substrate | specific activity [U/mg] | | |
|---|---|---|---|
| | EstCE1 | EstA3 | EstCL1 |
| pNP-butyrate ($C_4$) | 31.1 | 513.6 | n.d. |
| pNP-valerate ($C_5$) | 22.9 | 425.7 | n.d. |
| pNP-caproate ($C_6$) | 7.4 | 425.7 | 80.0 |
| pNP-octanoate ($C_8$) | 1.0 | 3.6 | n.d. |
| pNP-decanoate ($C_{10}$) | 0.9 | 0 | n.d. |
| pNP-palmitate ($C_{16}$) | 0.0 | 0 | n.d. |

Enzyme activities on the substrates triacetin, tripropionin, tributyrin, tricaprylene, trilaurin and vinyl-substrates (vinyl-acetate, ~propionate, ~butyrate, ~caproate, ~caprylate and ~laurate) were determined using a standard titration assay with minor modifications [25]. Tests were performed with a Methrom 718 STAT potentiometric titrator (Herisau, Switzerland) and by using 10 mM NaOH for titration. The substrates at 10 mM concentration were emulsified in 20 ml reaction buffer containing 2 mM Tris/HCl pH 7.0. After addition of 7.5 µg of the purified enzyme the NaOH consumption was recorded at a reaction temperature of 37° C. One unit was defined as the amount of enzyme that released 1.0 mmol of fatty acid per min.

Enzyme assays with these substrates confirmed the observation that only short chain substrates are converted by the enzyme according to SEQ ID NO: 4 (Tables 6+7).

TABLE 6

Activity of the enzymes with various triglycerides

| substrate | specific activity [U/mg] | | |
|---|---|---|---|
| | EstCE1 | EstA3 | EstCL1 |
| triacetin ($C_2$) | 26.7 | 147.5 | 120 |
| tripropionin ($C_3$) | 33.3 | n.d. | 200 |
| tributyrin ($C_4$) | 54.7 | 167.5 | 330 |
| tricaprylin ($C_8$) | 0 | n.d. | 0 |
| trilaurin ($C_{12}$) | 0 | n.d. | 0 |

(n.d. = not determined)

TABLE 7

Activity of the enzymes with various vinyl acid esters

| substrate | specific activity [U/mg] | | |
|---|---|---|---|
| | EstCE1 | EstA3 | EstCL1 |
| vinyl acetate ($C_2$) | 13.3 | 107.5 | 0 |
| vinyl propionate ($C_3$) | 13.3 | 380.0 | 173 |
| vinyl butyrate ($C_4$) | 16.0 | 387.5 | 550 |
| vinyl caproate ($C_6$) | 0 | 237.5 | n.d. |
| vinyl caprylate ($C_8$) | 0 | 155.0 | 80 |
| vinyl laurinate ($C_{12}$) | 0 | 7.5 | 0 |

The specific activity of the enzyme according to SEQ ID NO: 2 was significantly higher and this enzyme was capable of hydrolyzing substrates with a chain length of up to $C_{12}$ with the optimum at a chain length of $C_4$. The enzyme according to SEQ ID NO: 6 showed its chain length optimum also at $C_4$ with the highest activity of all enzymes of the present invention. These biochemical tests indicate that the enzymes belong to the esterase class of enzyme rather than to the lipases.

EXAMPLE 5

Determination of Solvent Stability

The stability of the enzymes was determined in the presence of the following solvents: DMSO, isopropanol, methanol, dimethylformamide, acetone and acetonitrile. The enzymes were incubated for 1 hour at 30° C. in the presence of either 15% (v/v) or 30% (v/v) of the solvents and the residual activity was measured at 45° C. The substrate used was pNP-butyrate.

The recombinant enzyme according to SEQ ID NO: 4 was quite stable in the presence of 15% (v/v) DMSO, methanol and isopropanol, retaining 103%, 90% and 75% residual activity, respectively. At the same concentration, dimethylformamide, acetone and acetonitrile strongly inhibited activity of the enzyme according to SEQ ID NO: 4 with the enzyme displaying only 34%, 14% and 0% residual activity, respectively. When this enzyme was tested against a higher concentration, 30% (v/v), of the solvents it was completely inhibited and only able to retain 17% and 23% activity in the presence of DMSO and isopropanol, respectively.

In contrast, the enzyme according to SEQ ID NO: 2 proved to be very stable, displaying increased activity in the presence of all the tested solvents. With 15% and 30% (v/v) DMSO it retained full activity at 102% and 104%, respectively. The enzyme activity was stimulated to the same level by both concentrations of dimethylformamide and acetone with activity measured at levels up to 128% and 155%, respectively. When the concentration of methanol was increased from 15% (v/v) to 30% (v/v) there was an increase in the activity of the enzyme according to SEQ ID NO: 2 from 111% to 130%. When concentrations were increased from 15% (v/v) to 30% (v/v) there was a decrease in the activity of the enzyme according to SEQ ID NO: 2 from 155% to 117% in the presence of isopropanol and from 110% to 87% in the presence of acetonitrile. The results are shown in Table 8.

TABLE 8

Residual activity of the enzymes after 1 h incubation in the presence of 15 or 30% (v/v) solvent

| solvent | EstCE1 | | EstA3 | | EstCL1 | |
|---|---|---|---|---|---|---|
| | 15% | 30% | 15% | 30% | 15% | 30% |
| none | 100 | 100 | 100 | 100 | 100 | 100 |
| DMSO | 103 | 17 | 102 | 104 | n.d. | n.d. |
| Methanol | 90 | 0 | 111 | 130 | n.d. | n.d. |
| Isopropanol | 75 | 23 | 155 | 117 | n.d. | n.d. |
| Dimethylformamid | 34 | 0 | 125 | 128 | n.d. | n.d. |
| Acetone | 14 | 0 | 152 | 155 | n.d. | n.d. |
| Acetonitrile | 0 | 0 | 110 | 87 | n.d. | n.d. |

EXAMPLE 6

Determination of Substrate Specificity

The substrate range of the two enzymes was determined using pNP esters of the following: benzoate, 2-(4-isobutylphenyl)propanoate (Ibuprofen), 2-phenylpropanoate, 3-phenylbutanoate, cyclohexanoate, 2-(3-benzoylphenyl) propanoate, 2-naphthoate, 1-naphthoate, adamantanoate and 2-(6-methoxynaphthalene-2-yl)propanoate (Naproxen). Activity was determined at 410 nm after 30 minute incubation at 40° C. The reaction mixture was 950 µl buffer (100 mM Tris, pH 7.5), 50 µl substrate (5 mg/ml in DMSO) and 1 µg enzyme. The results are shown in Table 9.

TABLE 9

Activity of the enzymes on pNP-substrates with importance for pharmaceutical products

| pNP-ester of ... | Specific activity [U/mg] | | |
|---|---|---|---|
| | EstCE1 | EstA3 | EstCL1 |
| benzoate | 12.1 | 9.4 | n.d. |
| 2-(4-isobutylphenyl) propanoate | 0 | 7.2 | n.d. |
| 2-phenylpropanoate | 0 | 21.0 | n.d. |
| 3-phenylbutanoate | 1.0 | 31.6 | n.d. |
| cyclohexanoate | 16.8 | 50.0 | n.d. |
| 2-(3-benzoylphenyl) propanoate | 0.8 | 26.7 | n.d. |
| 2-naphthoate | 0 | 0 | n.d. |
| 1-naphthoate | 0 | 0 | n.d. |
| adamantanoate | 0 | 0 | n.d. |
| 2-(6-methoxy-naphthalen-2-yl) propanoate | 0 | 26.7 | n.d. |

EXAMPLE 7

Enzyme Activity Fingerprinting with Substrate Cocktails

The enzyme activity fingerprinting used 10 substrates and was carried out as described previously [26]. The assay conditions were 75% PBS buffer at pH 7.4, 25% DMSO and 0.0025% SDS. Each substrate was present in the cocktail at 15 µM, the total concentration of the substrate cocktail was 150 µM. EstA3 was added at a concentration of 0.75 mg/L and EstCE1 at 0.2075 mg/L. The reaction time was 30 min. The chemical background was measured by recording the products observed under the same assay conditions after a 5 day incubation in the absence of the enzyme. The blank value was taken from the reaction after 30 min incubation in the absence of the enzyme. The results and the structures of the substrates are shown in FIG. 9.

EXAMPLE 8

Determination of Enantioselectivity

To assay the activity of the enzymes on a range of acetic acid esters gas chromatography was used. The samples were analyzed for the production of chiral alcohols by the gas chromatograph GC-17A (Shimadzu, Duisburg, Germany) equipped with FID detector and CP-Chirasil-DEX CB (Chrompack (Middelburg, Netherlands), 25 m×0.25 mm ID) at a helium flow of 1.3 ml/min. The temperature programme included: 5 min at 60° C., followed by an increase of 5° C. per min until 190° C. was reached. For the GC analysis, activity-tests were run in 1 M Tris buffered solutions and using 10 mM substrates dissolved in DMSO as 0.1 M stock solutions. 2 µg of the enzyme were added and tests incubated over night before the corresponding alcohols could be extracted by treatment with acetic acid ethyl ester and analyzed by GC. The results are shown in Table 10.

TABLE 10 activity of the enzymes against racemic or enantiopure compounds as judged by GC analysis

| | EstA3 | | | EstCE | | | EstCL1 | | | EstCl2 | | |
|---|---|---|---|---|---|---|---|---|---|---|---|---|
| | conversion % of | | | conversion % of | | | conversion % of | | | conversion % of | | |
| substrate | 1.e | 2.e | ee % | 1.e | 2.e | ee % | 1.e | 2.e | ee % | 1.e | 2.e | ee % |
| acetic acid ester of (+/−)-1-octin-3-ol | 24 | 18 | 12 | 64 | 60 | 3 | 0 | 0 | — | n.d. | n.d. | n.d. |
| acetic acid ester of cis-1,2-cyclohexandiol | 0 | 0 | — | 100[1] | 100[1] | 0 | n.d. | n.d. | n.d. | n.d. | n.d. | n.d. |
| acetic acid ester of trans-1,2-cyclohexandiol | 0 | 0 | — | 100 | 45 | 38 | n.d. | n.d. | n.d. | n.d. | n.d. | n.d. |
| Acetic acid ester of tetrahydronaphthylamin | 0 | 0 | — | 0 | 0 | — | 0 | 0 | — | n.d. | n.d. | n.d. |
| acetic acid ester of phenylethylamin | 0 | 0 | — | 0 | 0 | — | 0 | 0 | — | n.d. | n.d. | n.d. |
| acetic acid ester of R-(+)-3-chlor-1-phenyl-1-propanol | 6[2] | — | — | 100[2] | — | — | n.d. | n.d. | n.d. | n.d. | n.d. | n.d. |
| acetic acid ester of trimethylsilylbutinol | 45[2] | — | — | 100[2] | — | — | n.d. | n.d. | n.d. | n.d. | n.d. | n.d. |
| cis-3,5-diacetoxy-1-cyclopenten | 24 | 0 | 100 | 12 | 59 | 66 | 100 | 0 | 100 | 100 | 0 | 76.3 |
| isopropylidenglycerolacetate (rac.) | 0 | 0 | — | 100[1] | 100[1] | 0 | 0 | 35 | 100 | n.d. | n.d. | n.d. |
| menthylacetate (1. enantiomer (+), 2.e. (−)) | 0 | 0 | — | 100 | 0 | 100 | 0 | 0 | — | n.d. | n.d. | n.d. |

(e = enantiomer, n.d. = not determined)

[1] substrate conversion after 12 h,

[2] only complete conversion could be measured

EXAMPLE 9

Determination of pH-Optimum

The pH optimum for the enzymes was determined using tributyrin as substrate. The incubation conditions were 20 ml buffer (2.5 mM phosphate buffer [pH 4-7], 2.5 mM Tris/HCl buffer [pH 7-11] or 2.5 mM glycine buffer [pH 9-11], supplemented with 100 mM NaCl) stirred at a constant temperature of 37° C. The esterase substrate tributyrin (final concentration of 2 mM) was added to 5 ml of the corresponding buffer at 37° C., emulsified and added to the whole preparation. This substrate emulsion was held constant at the correct pH automatically by the titrator (718 STAT Titrino; Metrohm, Herisau, Switzerland) for 2 min and this served as the control. The enzymes were added separately to the emulsion and the consumption of 0.01 M NaOH was measured over 4 min, which allowed the calculation of the specific activity of each enzyme at various pH adjustments.

The activity of enzymes according to SEQ ID NOs: 2, 4 and 6 was tested under buffered conditions over the range pH 4 to 11. All enzymes displayed high activities under neutral to alkalophilic conditions with no activity below pH 6 for the enzyme according to SEQ ID NO: 6, below pH 5 for the enzyme according to SEQ ID NO: 4 and below pH 4 for the enzyme according to SEQ ID NO: 2. The highest activity was measured at pH 10 for the enzyme according to SEQ ID NO: 4, pH 9 for the enzyme according to Seq ID NO. 2 and pH 8 for the enzyme according to SEQ ID NO: 6 (FIG. 10). Surprisingly, the enzymes according to SEQ ID NOs: 2 and 4 were extremely stable with little loss of activity after incubation for up to 48 hours under alkaline conditions up to pH 12 (data not shown).

EXAMPLE 10

Determination of Temperature Optimum

The temperature range of the enzymes was tested using pNP-caproate as substrate. To determine the temperature optimum, the enzymes were tested at temperatures ranging from 25° C. to 70° C. as described above.

The enzymes according to SEQ ID NOs: 2 and 4 were active over a wide temperature range retaining a minimum of 50% relative activity between 37.6° C. and 55.8° C. for the enzyme according to the SEQ ID NO: 2 and between 36.3° C. and 51.2° C. for the enzyme according to the SEQ ID NO: 4 Maximum activity was measured at 47° C. and 50° C. for the enzyme according to the SEQ ID NOs: 2 and 4, respectively (FIG. 11). Both enzymes displayed similar overall activity patterns with a rapid decrease in activity when incubated at temperatures higher than their optimum.

EXAMPLE 11

Determination of Thermal Stability

To assay the thermostability of the enzymes they were incubated at different temperatures for one hour and the residual activity assayed at 10 minute intervals. Residual activity was measured using pNP-caproate as substrate as described above.

The enzymes according to the SEQ ID NO: 2 and 4 remained relatively stable at temperatures below 40° C. and could be incubated for at least 60 minutes without a major loss of activity at 40° C. (FIG. 12). However, incubation at temperatures above 45° C. for more than 60 minutes resulted in a rapid inactivation of both enzymes (data not shown).

REFERENCES

[1] Bommarius A. S. & Riebel B. R., 2004, Biocatalysis, Wiley-VCH, Weinheim, Germany

[2] Lorenz P. & Eck J., 2004, Screening for novel industrial biocatalysts, Engineering in Life Sciences, 4, 501-503

[3] Schmid A., Dordick J. S., Hauer B., Kiener A., Wubbolts M. & Witholt B., 2001, Industrial biocatalysis today and tomorrow, Nature 409, 258-268

[4] Ollis D. L., Cheah E., Cygler M., Dijkstra B., Frolow F., Franken S. M., Harel M., Remington S. J., Silman I., Schrag J., 1992, The alpha/beta hydrolase fold, Protein Eng., 1992, 5, 197-211

[5] Bornscheuer U., 2002, Microbial carboxyl esterases: classification, properties and application in biocatalysis, FEMS Microbiology Reviews, 26, 73-81

[6] Arpigny J. L. & Jaeger K.-E., 1999, Bacterial lipolytic enzymes: classificatiob and properties, Biochem J. 343, 177-183

[7] Pleiss J., Fischer M., Peiker M., Thiele, C., & Schmid R. D., 2000, Lipase engineering database: understanding and exploiting sequence-structure-function relationships, J Mol Catal B, 10, 491-508

[8] Henke E., Bornscheuer U. T., Schmid R. D. & Plaiss J., 2003, A molecular mechanisms of enantiorecognition of tertiary alcohols by craboxylesterases, ChemBioChem, 4, 485-493

[9] Henke E., Pleiss J., Bornscheuer U. T., 2002, Activity of lipases and esterases towards tertiary alcohols: insights into structure-function relationships, Angew Chem Int Ed Engl., 41, 3211-3213

[10] Wagner U. G., Petersen E. I., Schwab H., Kratky C., 2002, EstB from *Burkholderia gladioli*: a novel esterase with a beta-lactamase fold reveals steric factors to discriminate between esterolytic and beta-lactam cleaving activity, Protein Sci, 11, 467-478

[11] Schlacher A., Stanzer T., Osprian I., Mischitz M., Klingsbichel E., Faber K., Schwab H., 1998, Detection of a new enzyme for stereoselective hydrolysis of linalyl acetate using simple plate assays for the characterization of cloned esterases from *Burkholderia gladioli*, J Biotechnol., 62, 47-54

[12] Dröge M. J., Bos R., & Quax W. J., 2001, Paralogous gene analysis reveals a highly enantioselective 1,2-O-isopropylideneglycerol caprylate esterase of *Bacillus subtilis*, Eur. J. Biochem. 268, 3332-3338

[13] Brogden et al., Drugs, 18, 241-277 (1979)

[14] Chen C. S., Fujimoto Y, Girdaukas G., Sih C. J., 1982, Quantitative analyses of the biochemical kinetic resolutions of enantiomers, J. Am. Chem. Soc., 104, 7294-7299

[15] Chen C. S., Wu S., Girdaukas G., Sih C. J., 1987, Quantitative analyses of the biochemical kinetic resolutions of enantiomers 2: Enzyme catalysed esterification in water-organic solvents biphasic systems, J. Am. Chem. Soc., 109, 2812-2817

[16] Henke, E., and U. T. Bornscheuer. 2002. Esterases from *Bacillus subtilis* and *B. stearothermophilus* share high sequence homology but differ substantially in their properties. Appl Microbiol Biotechnol 60:320-6).

[17] Faber, K. 2000. Biotransformations in organic chemistry, 2 ed. Springer-Verlag, Berlin, Heidelberg, N.Y.)

[18] D. Talker-Huiber, J. Jose, A. Glieder, M. Pressing, G. Stubenrauch, H. Schwab., Esterase estE from *Xanthomonas vesicatoria* is an outer membrane protein capable of hydrolyzing long-chain polar esters, 2003, Appl Micriobiol Biotechnol, 61, 479-487

[19] Choo D W, Kurihara T, Suzuki T, Soda K, Esaki N. A cold-adapted lipase of an Alaskan psychrotroph, *Pseudomonas* sp. strain B11-1: gene cloning and enzyme purification and characterization, 1998, Appl Environ Microbiol., 64, 486-491.

[20] Y C Chuang, S F Chiou, J H Su, M L Wu, M C Chang., Molecular analysis and expression of the extracellular lipase of *Aeromonas hydrophila* MCC-2, 1997, Microbiology, 143, 803-812.

[21] W. R. Pearson and D. J. Lipman, Improved Tools for Biological Sequence Comparison, 1988, *Proc. Natl. Acad. Sci.*, USA 85; 2444-2448 ( )

[22] C. Kanz, P. Aldebert, N. Althorpe, W. Baker, A. Baldwin, K. Bates, P. Browne, A I. van den Broek, M. Castro, G. Cochrane, K. Duggan, R. Eberhardt, N. Faruque, J. Gamble, F. G. Diez, N. Harte, T. Kulikova, Q. Lin, V. Lombard, R. Lopez, R. Mancuso, M. McHale, F. Nardone, V. Silventoinen, S. Sobhany, P. Stoehr, M. A. Tuli, K. Tzouvara, R. Vaughan, D. Wu, W. Zhu and R. Apweiler, The EMBL Nucleotide Sequence Database, 2005, *Nucleic Acids Res.* 33, D29-D33

[23] D. A. Benson, I. K. Mizrachi, D. J. Lipman, J. Ostell, D. L. Wheeler, GenBank, 2005, *Nucleic Acids Res.* 33, D34-D38

[24] Entcheva, P., W. Liebl, A. Johann, T. Hartsch, and W. R. Streit, Direct cloning from enrichment cultures, a reliable strategy for isolation of complete operons and genes from microbial consortia. 2001. *Appl. Environ. Microbiol.* 67, 89-99.

[25] Eggert, T., G. Pencreac'h, I. Douchet, R. Verger, and K. E. Jaeger, A novel extracellular esterase from *Bacillus subtilis* and its conversion to a monoacylglycerol hydrolase., 2000, *Eur. J. Biochem.* 267, 6459-6469.

[26] Goddard, J.-P., and J.-L. Reymond, Enzyme activity fingerprinting with substrate cocktails., 2004, *J. Am. Chem. Soc.*, 126, 11116-11117

[27] Molnar, I., Schupp, T., Ono, M., Zirkle, R., Milnamow, M., Nowak-Thompson, B., Engel, N., Toupet, C., Stratmann, A., Cyr, D. D., Gorlach, J., Mayo, J. M., Hu, A., Goff, S., Schmid, J. and Ligon, J. M. The biosynthetic gene cluster for the microtubule-stabilizing agents epothilones A and B from *Sorangium cellulosum* So ce90, 2000, *Chem. Biol.*, 7, 97-109

[28] Petersen, E., Zuegg, J., Ribbons, D. W. and Schwab, H., Molecular cloning and homology modeling of protocatechuate 3,4-dioxygenase from *Pseudomonas marginata*, 1996, *Microbiol. Res.* 151, 359-370

[29] Uchida H., Shigeno-Akutsu Y., Nomura N., Nakahara T., Nakajima-kambe T., Cloning and sequence analysis of poly(tetramethylene succinate) depolymerase from *Acidovorax delafieldii* strain BS-3., 2002, *J. Biosci. Bioeng.* 93, 245-247

[30] Bentley, S. D., Chater, K. F., Cerdeno-Tarraga, A. M., Challis, G. L., Thomson, N. R., James, K. D., Harris, D. E., Quail, M. A., Kieser, H., Harper, D., Bateman, A., Brown, S., Chandra, G., Chen, C. W., Collins, M., Cronin, A., Fraser, A., Goble, A., Hidalgo, J., Hornsby, T., Howarth, S., Huang, C. H., Kieser, T., Larke, L., Murphy, L., Oliver, K., O'Neil, S., Rabbinowitsch, E., Rajandream, M. A., Rutherford, K., Rutter, S., Seeger, K., Saunders, D., Sharp, S., Squares, R., Squares, S., Taylor, K., Warren, T., Wietzorrek, A., Woodward, J., Barrell, B. G., Parkhill, J. and Hopwood, D. A., Complete genome sequence of the model actinomycete *Streptomyces coelicolor* A3(2), 2002, *Nature*, 417, 141-147

The invention claimed is:

1. An isolated or purified fusion polypeptide having carboxyl esterase activity, wherein the fusion polypeptide comprises: (a) an amino acid sequence that is at least 85% identical to the amino acid sequence of SEQ ID NO: 2, 4, 6, or 8 and (b) an amino acid sequence that is heterologous to the amino acid sequence of (a).

2. A composition comprising the fusion polypeptide of claim 1.

3. A method for converting rac-menthyl acetate to (+) menthol, comprising contacting rac-menthyl acetate with the fusion polypeptide of claim 1 to convert the rac-menthyl acetate to (+) menthol.

4. An isolated polynucleotide encoding the polypeptide of claim 1.

5. The polynucleotide of claim 4, wherein the heterologous amino acid sequence of (b) is a polypeptide selected from NusA, maltose binding protein or glutathione S-transferase.

6. A vector comprising the polynucleotide of claim 4.

7. An isolated host cell transformed or transfected with the polynucleotide of claim 4.

8. The polynucleotide of claim 4, wherein the polynucleotide comprises an expression control sequence.

9. The host cell of claim 7 which is a prokaryotic host cell selected from the group consisting of *E. coli*, *Bacillus* sp., *Pseudomonas* sp., *Streptomyces* sp., *Mycobacterium* sp., *Caulobacter* sp., *Rhodobacter* sp., *Lactococcus* sp., *Burkholderia* sp., *Rhizobium* sp., *Sinorhizobium* sp. and *Ralslonia* sp.

10. A process for producing a fusion polypeptide having carboxyl esterase activity, comprising culturing the host cell of claim 7 and recovering a fusion polypeptide produced by said host, wherein the fusion polypeptide comprises: (a) an amino acid sequence that is at least 85% identical to the amino acid sequence of SEQ ID NO: 2, 4, 6, or 8 and (b) an amino acid sequence that is heterologous to the amino acid sequence of (a).

11. The fusion polypeptide of claim 1, wherein the amino acid sequence of (a) is at least 90% identical to the amino acid sequence of SEQ ID NO: 2, 4, 6, or 8.

12. The fusion polypeptide of claim 1, wherein the amino acid sequence of (a) is at least 95% identical to the amino acid sequence of SEQ ID NO: 2, 4, 6, or 8.

13. The fusion polypeptide of claim 1, wherein the amino acid sequence of (a) is at least 97% identical to the amino acid sequence of SEQ ID NO: 2, 4, 6, or 8.

14. The fusion polypeptide of claim 1, wherein the amino acid sequence of (a) comprises the amino acid sequence of SEQ ID NO: 2, 4, 6, or 8.

15. The polynucleotide of claim 4, wherein the amino acid sequence of (a) is at least 90% identical to the amino acid sequence of SEQ ID NO: 2.

16. The polynucleotide of claim 4, wherein the amino acid sequence of (a) is at least 90% identical to the amino acid sequence of SEQ ID NO: 4.

17. The polynucleotide of claim 4, wherein the amino acid sequence of (a) is at least 90% identical to the amino acid sequence of SEQ ID NO: 6.

18. The polynucleotide of claim 4, wherein the amino acid sequence of (a) is at least 90% identical to the amino acid sequence of SEQ ID NO: 8.

19. A process for producing bacteria or eukaryotic cells capable of expressing a fusion polypeptide having carboxyl esterase activity, the process comprising transforming or transfecting bacteria or eukaryotic cells with the vector of claim 6.

* * * * *